United States Patent
Han et al.

(10) Patent No.: US 11,659,855 B2
(45) Date of Patent: May 30, 2023

(54) EMULSIONS AND DERIVATIVES FOR INFUSING HYDROPHOBIC ACTIVE AGENTS INTO AN EDIBLE PRODUCT

(71) Applicant: Vertosa Inc., Walnut Creek, CA (US)

(72) Inventors: Chunxiao Han, Walnut Creek, CA (US); Lauren Tamburro, Walnut Creek, CA (US)

(73) Assignee: Vertosa Inc., Walnut Creek, CA (US)

( * ) Notice: Subject to any disclaimer, the term of this patent is extended or adjusted under 35 U.S.C. 154(b) by 0 days.

(21) Appl. No.: 17/810,440

(22) Filed: Jul. 1, 2022

(65) Prior Publication Data

US 2022/0346426 A1 Nov. 3, 2022

Related U.S. Application Data

(63) Continuation of application No. PCT/US2022/071894, filed on Apr. 25, 2022.

(60) Provisional application No. 63/180,371, filed on Apr. 27, 2021.

(51) Int. Cl.
| | |
|---|---|
| *A23L 33/105* | (2016.01) |
| *A61K 31/352* | (2006.01) |
| *A61K 47/36* | (2006.01) |
| *A61K 9/107* | (2006.01) |
| *A61K 47/42* | (2017.01) |
| *A61K 9/68* | (2006.01) |

(52) U.S. Cl.
CPC .......... *A23L 33/105* (2016.08); *A61K 9/0058* (2013.01); *A61K 9/107* (2013.01); *A61K 31/352* (2013.01); *A61K 47/36* (2013.01); *A61K 47/42* (2013.01)

(58) Field of Classification Search
None
See application file for complete search history.

(56) References Cited

U.S. PATENT DOCUMENTS

| | | |
|---|---|---|
| 2019/0015383 A1 | 1/2019 | Woelfel et al. |
| 2019/0022055 A1 | 1/2019 | Siegel et al. |
| 2020/0397015 A1 | 12/2020 | Yiannios et al. |

FOREIGN PATENT DOCUMENTS

WO 2021046295 A1 3/2021

OTHER PUBLICATIONS

"Easy DIY Cannabis Infused Gummies" (Web page dated Apr. 4, 2019), retrieved from the internet on Jun. 14, 2022Jun. 2014. URL: web.archive.org/web/20190404194940/https:/gethighlikealady.com/new-blog/diy-marijuanagummies.>.

Ewell, Taylor Russell, et al. "Pharmacokinetic Investigation of Commercially Available Edible Marijuana Products in Humans: Potential Influence of Body Composition and Influence on Glucose Control." Pharmaceuticals 14.8 (2021): 817.

*Primary Examiner* — Michael V Meller
(74) *Attorney, Agent, or Firm* — Plant & Planet Law Firm

(57) ABSTRACT

Provided are edible products infused with an emulsion containing one or more active agents.

5 Claims, 4 Drawing Sheets

EMULSIONS AND DERIVATIVES FOR INFUSING HYDROPHOBIC ACTIVE AGENTS INTO AN EDIBLE PRODUCT

CLAIM OF PRIORITY UNDER 35 U.S.C. § 119

The present application for patent is a bypass continuation of International Application No. PCT/US2022/071894, entitled "EMULSIONS AND DERIVATIVES FOR INFUSING HYDROPHOBIC ACTIVE AGENTS INTO AN EDIBLE PRODUCT," filed on Apr. 25, 2022, which in turn claims priority to Provisional Application No. 63/180,371, entitled "EMULSIONS AND DERIVATIVES FOR INFUSING HYDROPHOBIC ACTIVE AGENTS INTO AN EDIBLE PRODUCT," filed Apr. 27, 2021, both of which are hereby expressly incorporated by reference herein.

BACKGROUND

Field

This invention relates to edible products infused with an emulsion containing one or more active agents.

Background

Edible *Cannabis* products are becoming increasingly popular. Such products avoid the unhealthy effects of smoking and can deliver cannabinoids efficiently and reliably in a discrete manner.

SUMMARY

Some embodiments of the invention relate to an edible product infused with an emulsion composition. The product can include a base and an emulsion composition. The emulsion composition can include one or more active agents, an emulsifier, a carrier oil, and/or water. In some embodiments, the emulsifier can be *Quillaja* extract and/or gum acacia.

In some embodiments, the carrier oil can be at least 1 time of the cannabinoid and the emulsifier can be at least 0.05 times the total amount of the carrier oil and the one or more active agent.

In some embodiments, the product can have a main active agent and the product can have a time to peak drug concentration (Tmax) of the main active agent and metabolites of the main active agent of less than 120 minutes.

In some embodiments, the product can have an onset time of an effect of the one or more active agents of less than 20 minutes on an empty stomach.

In some embodiments, the product is a gummy candy or a "gummy."

In some embodiments, the base can include gelatin, pectin, and/or the like.

Some embodiments of the invention relate to a method of making the product described herein. The method can include one or more of: (a) mixing gelatin or pectin and water at a temperature sufficient to dissolve the gelatin or pectin, (b) optionally adjusting the Brix to 70-85° Bx, (c) cooling the solution to less than 215° F. (d) adding the emulsion composition described herein, (e) optionally adding flavor, and or (f) depositing and curing the solution to obtain a gummy candy. In some embodiments, the wherein the final product has potency homogeneity throughout.

In some embodiments, the potency of the cannabinoid can remain substantially similar once incorporated into the final product.

In some embodiments, step (a) can include mixing pectin and the water in step (a) can be first is mixed with less than 0.1% of sodium citrate or other buffering agent In some embodiments, the product can be a candy, chewing gum, baked good, cacao product, frozen confectionery, beverage, health bar, nutrition bar, mint, cough drop, pharmaceutical formulation, and/or the like.

In some embodiments, the product can be a hard candy, soft candy, gummy, candy bar, liquid filled soft candy, cookie, brownie, chocolate product, cocoa product, ice cream, ice pop, pharmaceutical gel capsule, pharmaceutical soft gel, pharmaceutical tablet, and/or the like.

DETAILED DESCRIPTION

Figure 1:
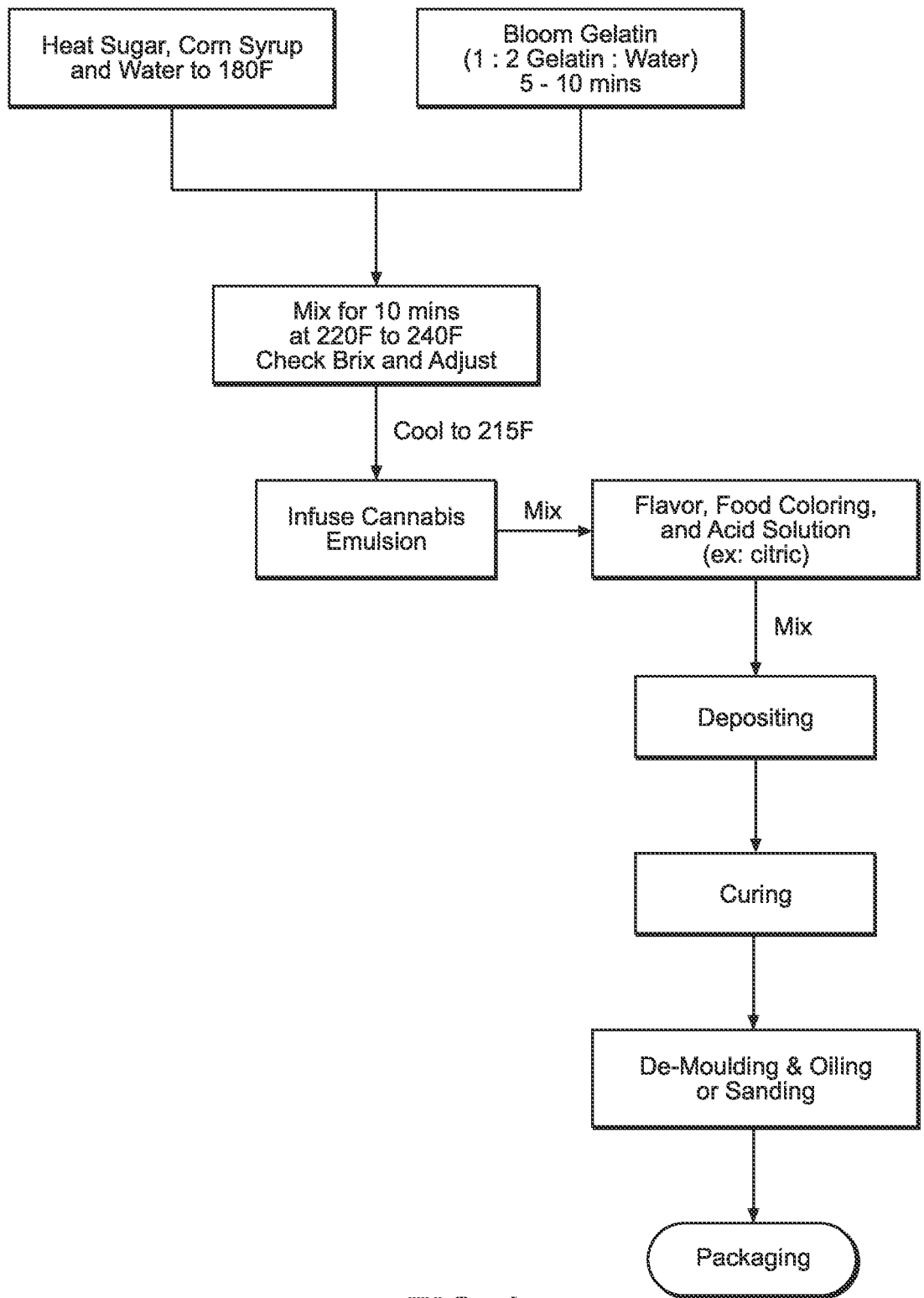
FIG. 1 is a depiction of a method that can be used to prepare an edible product of the invention.

Edible products containing a base and an emulsion composition are provided. The emulsion composition can have one or more active agents so that when incorporated/infused with a base product, an infused product with the one or more active agents is obtained.

As used herein, an infused product is a product that has been incorporated with another product. The emulsion infused product described herein is a product where the emulsion has been incorporated into the product. The incorporation can be done by mixing a base product with the emulsion in a liquid solution or any other similar method.

The base product can include, but is not limited to, a base for preparing a chewy product (also referred to herein in the singular as a "gummy" and in the plural as "gummies"), condiment, candy, cough drop, ice cream, ice pop, chewing gum, chewy candy with a juice center (e.g., Gushers™), cosmetic, and/or the like.

The emulsion composition can include a nano-emulsion or a micro-emulsion.

The emulsion can include one or more of a hydrophobic active agent, a carrier oil, a main emulsifier, a co-emulsifier, water, and/or other additional ingredients such as those listed in the following formula in Table 1.

TABLE 1

| Hydrophobic Active Agent | Carrier Oil | Main Emulsifier | Optional Co-Emulsifier | Water | Optional Preservative or Stabilizer | Total Weight |
|---|---|---|---|---|---|---|
| a | b | c | d | e | f | g = (a + b + c + d + e + f) |

The term "emulsion," as used herein, can refer to a mixture of two or more liquids that are not usually miscible or soluble with one another.

The emulsion technology can include one or more hydrophobic active agents (or "actives") into an aqueous base product. An active agent or an "active" can be defined as a molecule or a set of molecules capable of modifying or modulating a biological system. The term "active agent" as used herein, can refer to a substance that can produce a chemical reaction.

The term "emulsifier" as used herein, can refer to a substance that can stabilize the emulsion.

The hydrophobic active agent can be a cannabinoid, a terpene, an essential oil, a flavonoid, a polyphenol, and any combination thereof. Where this application describes a cannabinoid, other active agents can be used instead of or in addition to the cannabinoid.

Exemplary cannabinoids can include, but are not limited to tetrahydrocannabinolic acid A (THCA-A), tetrahydrocannabinolic acid B (THCAB), tetrahydrocannabinol (THC), tetrahydrocannabinolic acid C (THCA-C), tetrahydrocannabinol C (THC-C), tetrahydrocannabivarinic acid (THCVA), tetrahydrocannabivarin (THCV), tetrahydrocannabiorcolic acid (THCA-C), tetrahydrocannabiorcol (THC-C), delta-7-cis-iso-tetrahydrocannabivarin, delta-8-tetrahydrocannabinolic acid (Δ8-THCA), delta-9-tetrahydrocannabinol (Δ9-THC), cannabidiolic Acid (CBDA), cannabidiol (CBD), cannabidiol monomethylether (CBDM), cannabidiol-C(CBD-C), cannabidivarinic acid (CBDVA), cannabidivarin (CBDV), cannabidiorcol (CBD-C), cannabigerolic acid (CBGA), cannabigerolic acid monomethylether (CB GAM), cannabigerol (CB G), cannabigerol monomethylether (CBGM), cannabigerovarinic Acid (CBGVA), cannabigerovarin (CBGV), cannabichromenic Acid (CBCA), cannabichromene (CBC), cannabichromevarinic Acid (CBCVA), cannabichromevarin (CBCV), cannabicyclolic acid (CBLA), cannabicyclol (CBL), cannabicyclovarin (CBLV), cannabielsoic acid A (CBEA-A), cannabielsoic acid B (CBEA-B), cannabielsoin (CBE), cannabinolic acid (CBNA), cannabinol (CBN), cannabinol methylether (CBNM), cannabinol-C4 (CBN-C4), cannabivarin (CBV), cannabinol-C(CBN-C), cannabiorcol (CBN-C1), cannabinodiol (CBND), cannabinodivarin (CBVD), cannabitriol (CBT), 10-Ethoxy-9-hydroxy-delta-6a-tetrahydrocannabinol, 8,9-dihydroxy-delta-6a-tetrahydrocannabinol (8,9-Di-OH-CBT-C5), cannabitriolvarin (CB TV), ethoxy-cannabitriolvarin (CBTVE), dehydrocannabifuran (DCBF), cannabifuran (CBF), cannabichromanon (CBCN), cannabicitran (CBT), 10-oxo-delta-6a-tetrahydrocannabinol (OTHC), delta-9-cis-tetrahydrocannabinol (Δ9-cis-THC), cannabiripsol (CBR), -3,4,5,6-tetrahydro-7-hydroxy-alpha-alpha-2-trimethyl-9-n-propyl-2,6-methano-2H-1-benzoxocin-5-methanol (OH-iso-HHCV), trihydroxy-delta-9-tetrahydrocannabinol (triOH-THC), an isocanabinoid, any other cannabinoid, and any combination thereof.

Exemplary terpenes can include, but are not limited to, myrcene, limonene, linalool, beta-caryophyllene, alpha-pinene and beta-pinene, alpha-bisabolol, eucalyptol, trans-nerolidol, humulene, delta-3-carene, camphene, borneol, terpineol, valencene, geraniol, eugenol, sabinene, phellandrene, borneol, isoborneol, phytol, menthol, geraniol, citronellol, ocimene, halomon, thymol, carvacrol, thujene, camphene, camphor, verbenone, botrydial, ngaione, cuparane, labdane, ferruginol, cafestol, any other terpene, and any combination thereof.

Exemplary essential oils can include but are not limited to vitamin E; vitamin B12; vitamin A; vitamin D; vitamin B; omega 3; astaxanthin; fish oil; medium chain triglyceride (MCT) oil; long chain triglyceride (LCT) oil; cannabinoid(s) in MCT; coconut oil; palm oil; eicosapentaenoic acid (EPA); docosahexaenoic acid (DHA); essential oils such as but not limited to lemon oil, orange oil, peppermint oil, Ylang-Ylang oil, lemongrass oil, tea tree oil, rosemary oil, Australian sandalwood oil, grapefruit oil, frankincense oil, cedarwood oil, patchouli oil, cinnamon bark oil, bergamot oil, chamomile oil, lemon-*eucalyptus* oil, ginger oil, key lime oil, vanilla oil, clove oil; any other essential oil; and any combination thereof.

Exemplary flavonoids can include, but are not limited to cannflavin A, cannflavin B, cannflavin C, orientin, quercetin, silymarin, kaempferol, apigenin, any other flavonoid, and any combination thereof.

Exemplary polyphenols can include, but are not limited to cannabism B, caffcoyltyramine, canniprene, any other polyphenol, and any combination thereof.

Exemplary carrier oils can include, but are not limited to, sunflower oil, olive oil, coconut oil, sesame oil, avocado oil, palm oil, soybean oil, corn oil, peanut oil, canola oil, grape seed oil, corn oil, hazelnut oil, rice bran oil, linseed oil, safflower oil, sesame oil, passion fruit oil, lard, butter, cheese, animal fat, medium chain triglyceride (MCT) oil, long chain triglyceride (LCT) oil, cannabinoid(s) in MCT, vitamin E, vitamin B12, vitamin A, vitamin D, vitamin B, omega 3, astaxanthin, fish oil, eicosapentaenoic acid (EPA), docosahexaenoic acid (DHA), any other carrier oil, and any combination thereof.

The emulsifier can include *Quillaja* extract (e.g., Q-Naturale®), gum acacia, polyglyceryl-10 dipalmitate, and/or any combination thereof. Where there is more than one emulsifier, the emulsifier that is present in a larger amount can be referred to as the "main emulsifier" and other emulsifier(s) can be referred to as (a) co-emulsifier(s). Likewise, when more than one active agent is present, the active agent present in the largest amount can be referred to as the "main active agent."

The main emulsifier can include *Quillaja* extract (e.g., Q-Naturale®), gum acacia, polyglyceryl-10 dipalmitate, and/or any combination thereof.

The co-emulsifier can include *Quillaja* extract, polysorbate, polyglycerol (10-2-P), gum acacia, Q-Naturale®, vitamin E TPGS, lecithin, sucrose ester, any other emulsifier, and/or any combination thereof.

Some embodiments of the invention relate to a "*Quillaja* extract *Cannabis* emulsion" or a "*Quillaja* extract-based *Cannabis* emulsion" or a "*Quillaja* based *Cannabis* emulsion" wherein the emulsion includes *Quillaja* extract as the main emulsifier and an active agent found in *Cannabis*. Some embodiments of the invention relate to a "gum acacia *Cannabis* emulsion" or a "gum acacia-based *Cannabis* emulsion" wherein the emulsion includes gum acacia as the main emulsifier and an active agent found in *Cannabis*.

Commercially available *Quillaja* extract, such as E 999, is obtained by aqueous extraction of the milled inner bark or wood of *Quillaja saponaria*, other *Quillaja* species, or trees of the family Rosaceae. It contains a number of triterpenoid saponins consisting of glycosides of quillaic acid.

*Quillaja* extract or *quillaia* extract is a natural ingredient with potential to be used in products that can be organically certified. Other names include Murillo bark extract, Panama bark extract, Quillay bark extract, and Soapbark extract.

Ingredion® is the main supplier of *Quillaja* extract, where their commercial name is Q-Naturale®, which is a 20% *Quillaia* extract water solution. There are 4 major types of Q-Naturale® that offer different features such as preservative, organic certification, vegan certification, and natural sediment. Table 2 summarizes these types.

TABLE 2

| Q-Naturale ® types and their features | | | | | |
|---|---|---|---|---|---|
| | Code | Preservative | Organic | Vegan | Sediment |
| Q-Naturale ® | 100 | Yes | No | No | Less |
| | 200 | No | No | No | Less |
| | 200V | No | No | Yes | Heavy |
| | 300 | No | Yes | No | Less |

*Quillaja* extract can also be delivered in other commercial products such as SAPNOV™ series from Naturex® and Q Ultra® or QDP Ultra® series from Desert King™. *Quillaja* extract can be obtained in a dry powder form or an aqueous form. The dilution factors for either form factor depends on the active content of the *Quillaja* extract.

The optional additional ingredients can include preservatives or stabilizers, antioxidants, pH modulators, flavor agents, coloring agents, and/or the like.

Exemplary preservatives or stabilizers can include but are not limited to ethyl lauroyl arginate, sodium bi-sulphite, potassium benzoate, potassium sorbate, ascorbic acid, citric acid, benzoic acid, sodium benzoate, calcium ascorbate, erythorbic acid, sodium ascorbate, sorbic acid, *sulphurous* acid, calcium sorbate, vitamin E, any other preservative, and/or any combination thereof.

In some embodiments, the antioxidant can be a vitamin. Vitamins can include, but are not limited to, vitamin A (retinol), vitamin C (ascorbic acid), and vitamin E (tocopherol). In some embodiments, the antioxidant can be a carotenoid terpenoid such as, but not limited to, alpha or beta carotene, astaxanthin, cryptoxanthin, lutein, lycopene, zeaxanthin, or canthaxanthin; phenolic acids and their esters, such as, but not limited to, chicoric acid, chlorogenic acid, cinnamic acid, ellagic acid, ellagitannins, gallic acid, salicylic acid, rosmarinic acid, and gallotannins; nonflavonoid phenolics such as, but not limited to, curcumin, flavonolignans, xanthones, or eugenol; and/or flavonoids such as, but not limited to flavones, flavonols, flavanones, stilbenoids, isoflavone phytoestrogens, and anthocyanins. Other non-limiting examples of antioxidants can include capsaicin, bilirubin, citric acid, oxalic acid and phytic acid, EDTA, TBHQ, BHA, BHT, propyl gallate, and/or the like. In some embodiments, the antioxidant can be any commercially available antioxidant such as, for example, Brew Shield®, Structuan®, rosemary extract, and/or the like (e.g., Herbalox® (41.19.32) provided by Kalsec®).

Exemplary pH modulators can include but are not limited to citric acid, ascorbic acid, fumaric acid, lactic acid, phosphoric acid, acetic acid, malic acid, tartaric acid and/or any combinations thereof.

Exemplary food colors can include but are not limited to blue, green, red, purple, orange, and/or the like.

Exemplary flavoring agents can include but are not limited to honey, agave, caramel, an essential oil, a bitter blocker (e.g., ((3-[1-[(3,5-dimethylisoxazol-4-yl)methyl] pyrazol-4-yl]-1-[(3-hydroxyphenyl)methyl]imidazolidine-2,4-dione), GG-605-390-4, NP-844-232-9, QJ-6 15-696-6, TruClear™, *stevia*, and/or the like), a terpene, an artificial flavor agent (e.g., mint, orange, strawberry, cherry, and/or the like), and/or the like. Such ingredients can improve the taste and appearance of the composition.

As used herein, the Brix measurement refers to the amount of dissolved solid in a liquid. The Brix measurement of the product can be about 70-85° Bx (e.g., 70, 71, 72, 73, 74, 75, 76, 77, 78, 79, 80, 81, 82, 83, 84, 85 or more or less).

The edible product can be in the form of a pill, tablet, capsule, oblong tablet, sprinkle, aerosol, powder, liquid, gel, solid, and/or a combination of any of the same.

The edible product can be a candy (e.g., hard candy, soft candy, gummy, candy bar, liquid filled soft candy), chewing gum, baked good (e.g., cookies, brownies), cacao or cacao products (e.g., chocolate, cocoa), frozen confectionery (e.g., ice cream, ice pop), beverages, health bar or nutrition bar, mint, cough drop, pharmaceutical formulation (e.g., gel capsule, soft gel, tablet), any product described herein and/or the like.

Embodiments of the invention relate to methods for preparing the edible product. The method can include one or more steps of:
1. Batching
2. Cooking
3. Infusing
4. Depositing
5. Curing or Conditioning
6. Demolding
7. Coating
8. Packaging As used herein, batching can refer to the preparation of ingredients. Preparation can include weighing the ingredients to obtain a desired amount.

As used herein, cooking can refer to heating ingredients in one or more steps. As an example, a gelling agent can be bloomed with water while sugar and corn syrup are heated separately. Afterward, these ingredients can be combined and further cooked to remove moisture. As used herein, blooming with water can refer to soaking the gelling agent in water before use. The blooming step can require room temperature water or chilled water (e.g., <20° C.). First, the gelling agent can be weighed into a container, and water can be added into the gelling material with mild stirring and/or agitation. In some embodiments, the water may not be enough to fully dissolve the material but can wet it and cause it to expand and gel. This process can take up to 5 minutes during small scale production (<about 5 kg) or can take up to 30 minutes to 1 hour during large scale production (>5 kg about batch).

As used herein, blooming can mean to re-hydrate. Blooming is a test to measure the strength of a gel, gelling agent, or gel product. Blooming can range between 30-325, with a low bloom being in the 20-125 range, a medium bloom being in the 175-225 range, and high bloom being in the 225-325 range. The higher the bloom, the higher the melting and gelling points of a gel and the shorter time it takes the gel to set. A higher bloom strength gelatin will have a firmer texture and a shorter bite. A lower bloom strength gelatin will be softer and chewier.

As used herein, infusing can refer to adding the emulsion to the product base.

As used herein, depositing can refer to transferring a cooked solution into a mold. In some embodiments, starch or silicon molds can be used. Starch molds can be made by filling a tray with corn starch. Then a shape can be impressed into the starch to create the mold. In some embodiments, applying an oil, such as medium chain triglyceride (MCT) oil, into the molds before depositing can prevent sticking between the shape and the starch.

As used herein, curing or conditioning can refer to allowing the solution to set. The curing or conditioning step can occur for a period of time sufficient to allow the product to move from a liquid to a solid. The period of time can be 2, 4, 6, 10, 12, 14, 18, 20, 22, 24, 26, 28, 30, 32, 34, 36, 38, 40, 42, 44, 46, 48, or more hours. The curing or conditioning can occur at room temperature (e.g., about 65-72° F.) and relative humidity at 25% or below (e.g., 24%, 22%, 20%, 18%, 16%, 14%, 12%, or lower).

As used herein, demolding can refer to removing the solidified product from the molds.

As used herein, coating can refer to applying a coat to the solidified product. The coat can be capable of preventing the products from sticking together, creating a glossy appearance, and/or any other desired effect. As an example, the solidified product can be coated in a sugar mixture (also referred to as sanding) and/or can be coated in an oil, such as but not limited to carnauba wax and beeswax in MCT oil (also referred to as oiling).

As used herein, packaging can refer to packaging a final product. The packaging can be any container such as a wrapper, bottle, box, bag, and/or the like.

Advantages of infusing the emulsion, compared to infusing a distillate, as is common in the art, include:
1. Ease of production
2. Potency homogeneity
3. Quick onset
4. Customizable effect/experience When infusing distillate into a gummy, high heat and vigorous stirring is often required to blend oil soluble distillate into water soluble gummy base. When infusing the *Cannabis* emulsion into the gummy base, the two materials can be homogenized easily into one phase under mild agitation due to the high affinity between them. This makes the gummy production and infusion step easy on the operation.

Potency homogeneity refers to the homogeneity of the potency of the active agent(s) throughout the product. A product with potency homogeneity will have substantially similar potency among individual pieces throughout the whole batch that was infused with the emulsion composition In contrast, a product without substantially similar potency homogeneity can have potency "hot spots," where potency varies among individual pieces throughout the batch. As used herein, substantially similar can be defined as greater than 80, 85, 90, 95, 96, 97, 98, or 99 percent similarity. Thus, in some embodiments, a product with potency homogeneity can have more than 80, 85, 90, 95, 96, 97, 98, or 99 percent similarity throughout the product.

As used herein potency can be defined as the concentration of the active agent(s).

Onset, as used herein, can refer to the duration of time it takes for the effect of the active agent to come into prominence upon consumption of the edible product. In some embodiments, the onset can be 60, 50, 40, 30, 20, 10 minutes, or less. The onset can be affected by the state of the user's stomach, for example, the onset can be about 10 mins with an empty stomach and about 20 minutes with a full stomach.

The active agent(s) can be selected based on the desired "experience" Consumption of *Cannabis* by a human generally results in a wide variety of psychotropic effects, but which is often referred to as a "high." The *Cannabis* high varies depending on many factors, including the strain of *cannabis*, the amount consumed, the method of consumption, the biochemistry of the individual consuming it and the individual's level of experience in consuming *cannabis*. That said, a *Cannabis* high can include euphoria, anxiety, a general alteration of conscious perception, feelings of well-being, relaxation or stress reduction, increased appreciation of humor, music (especially discerning its various components/instruments) or the arts, joviality, metacognition and introspection, enhanced recollection (episodic memory), increased sensuality, increased awareness of sensation, increased libido, and creativity. Abstract or philosophical thinking, disruption of linear memory and paranoia or anxiety are also typical effects. The specific experience can be designed by blending different active agents at specific ratios. This can be done by mixing different active agents into one oil phase and processing this emulsion using a single emulsifier. Alternatively, different actives can be produced into different emulsions, where the same or different emulsifiers can be applied. The resulting emulsions with different active agents can be measured and combined to certain ratios for a targeted effect, which can be packaged into a product and sold to enhance different real-life experiences.

The effect and/or experience of the active agent can include pain relief, insomnia relief, increased energy, calming effect (e.g., decreased anxiety and/or stress), increase relaxation, increased creativity, changes in mood, changes in demeanor, and the like. For example, the active agent can induce a calming effect or an uplifting effect on a user. The effect and/or experience can be customized by selecting specific active agents in combination. For example, among other effects, CBD can bring about a relaxing effect, CBN can help with quicker sleep onset, CBG can be used for pain relief. As known in the art, the entourage effect can be achieved with various combinations of cannabinoids and/or terpenes.

To obtain a predictable effect and/or experience, the type and ratio of cannabinoids, and/or terpenes, and/or any active agent need to be accurately achieved in each product unit. This accuracy is a challenge when using a distillate to infuse a product such as a gummy. One reason is that different cannabinoids and terpenes need to be melted above their melting points (e.g., some at 90° C., some at 60° C.). Also, certain terpenes are very volatile and will evaporate quickly when infused into a hot mixture. Another reason is that when measuring the high purity input, it is very challenging to accurately target the ratio. As is demonstrated in the Examples below, the instant invention overcomes these challenges.

Processing conditions, primarily temperature and time at that temperature, from the lab to production can change. In some embodiments, a product is prepared first with 10-15% overage of active agent content in the pilot run. The product is then tested for potency and the amount of active agent is reduced to achieve the desired amount.

Embodiments of the invention relate to the production of various edible products infused with the emulsion described herein. In general, the emulsion can be added to a "base" product. The base product can be an existing product or an intermediate product of an existing product.

Some embodiments of the invention relate to methods of producing a *Quillaja* extract- or gum acacia-based cannabinoid emulsions that can be infused into general edible products (in addition to gummies). The method can include preparing a raw mixture. A cannabinoid distillate or isolate can be first dissolved into a carrier oil, such as MCT or LCT oil as an oil phase. The *Quillaja* extract or gum acacia can be dissolved in water and this water phase can be combined with the oil phase under either high shear mixing or ultrasonication. The raw mixture can include the carrier oil, the cannabinoid, the emulsifier and the water. The raw mixture can be processed through a high-pressure homogenizer, such as one from Best Emulsifying Equipment (BEE) International™ Microfluidics International Corporation™, Dyhydromatics®, GEA® Group, SPX-Flow or other suppliers. The desired *Quillaja* extract emulsion can be produced under different combinations of conditions such as but not limited to 10,000-45,000 PSI for 1-5 passes. Higher PSI and a greater number of passes can help get the droplet size to be smaller. The smallest size relates to the *Quillaja* extract and oil load ratio. When increasing the ratio of *Quillaja* extract to load oil, the droplet can be smaller, but it may also negatively impact the infused product's flavor.

In some embodiments, the carrier oil is 0.25 times-25 times (e.g., 0.25, 0.3, 0.35, 0.4, 0.45, 0.5, 0.6, 0.7, 0.8, 0.9 1, 2, 5, 7, 10, 12, 15, 17, 20, 22, or 25 times) of the active agents. In some embodiments, the carrier oil is at least 0.5 times the cannabinoids.

In some embodiments, the main emulsifier, depending on its surface activity and size, can be between 0.05 times to 5 times (e.g., 0.05, 0.5, 1, 1.5, 2, 2.5, 3, 3.5, 4, 4.5, or 5) the total amount of active agent(s) and carrier oil. In some embodiments, the *Quillaja* extract or gum acacia, is at least 0.05 times the total amount of the carrier oil and cannabinoids.

Hydrophobic drugs, such as cannabinoids and terpenes, are mainly absorbed through the epithetical cell in small intestines. In order for cannabinoids and terpenes to be absorbed, they need to be in the form of "mixed micelles", which include micelle (5-10 nm) and vesicle (100 nm). Mixed micelles can be constructed with fatty acids, monoglycerides, bile salts and phospholipids. Bile Salts and phospholipids are generated within human body during food consumption. Fatty acid and monoglyceride usually comes from consuming food with high fat content, such as plant oil or animal products. This is why consuming food has big impact on the total bioavailability of the *cannabis*-infused edible product.

It is important to build in good amount and type of fat into the emulsion, thus in the infused product, to help with the absorption of the cannabinoids. MCT is most ideal for providing good fatty acids and monoglycerides as raw ingredient for mixed micelles. LCT can be helpful in the formation of chylomicron, which helps deliver the cannabinoids into lymph system and bypassing liver, which is critical for controlling experience. Other carrier oil system, such as mineral oil or flavor oil, would not offer help on the absorption. The ideal range of MCT can be at least 1.5-5 times the amount of cannabinoids. The ideal range of LCT can be at least 2-5 times the amount of cannabinoids.

Drug (active agent) absorption via the oral mucosa is a passive diffusion process. By simplifying the oral mucosa into a hydrophobic membrane, Fick's first law can be used to describe the drug absorption process (equations 1 and 2):

$$P = D \times Kp/h$$

$$A = P \times C \times S \times = D \times Kp \times C \times S \times t/h,$$

where P is permeability coefficient, A is the amount of drug absorbed, D is the diffusion coefficient of the drug in the oral mucosa, Kp is the partition coefficient of the drug between delivery medium and the oral mucosa, h is the thickness of the oral mucosa, C is the free drug concentration in the delivery medium, S is the surface area of the delivery site on the oral mucosa and t is the duration of drug contacting the oral mucosa. If D and Kp are determined by the drug molecule, h is a number that cannot change, then to ensure a higher of total amount of drug absorbed (A), the drug concentration (C) needs to be high, the drug's shape needs to provide the highest surface area (S) and the drug needs to stay inside the mouth for enough long period (t).

"Gummies"

Gummies can include about 80% sugar and corn syrup; 2-8% gelling agent such as starch, gelatin, or pectin; less than 1% flavor, acid (e.g., tartaric, citric, or malic); and/or color. These are generalizations as there have been numerous gummies introduced to the market recently, including ones with various hydrocolloids, tapioca syrup, sunflower oil, juice concentrates, and the like.

In some embodiments, the gummy can have more corn syrup than sugar in the formulation to prevent "graining." Graining occurs when the sugar becomes super saturated and crystallizes, which causes what should be a transparent product to become opaque. In some embodiments, there can be at least a 5% difference between the amount of corn syrup and sugar. For example, if the formula has 40% corn syrup, then no more than 35% sugar is used.

There are two major types of gummies: gelatin-based and pectin-based. The advantages and disadvantages of each type are provided in the table below.

TABLE 3

| | Pros | Cons |
| --- | --- | --- |
| Gelatin | Thermally easy to work with thermally Reversible Transparent finished product | Animal derived Easy to melt due to high temperature |
| Pectin | Vegan Plant derived Retains shape when exposed to high temperature | Hard to work with Not thermally reversible |

A depiction of a method that can be used to prepare the edible product is provided in FIG. 1. The "01 emulsion" or "Organic 1" refers to an emulsion comprising *Quillaja* extract as the emulsifier and MCT oil as the carrier oil.

The method can include a cooking step wherein the gelling agent can be bloomed with water while the sugar and corn syrup are heated separately. Afterward, these ingredients can be combined and cooked to remove moisture. Following this, the emulsion can be infused into a product.

For a gelatin-based product, the emulsion can be infused into the product immediately after the sugar, corn syrup, gelling agent, and water have been removed from heat. Following this, the flavors, colors, and acid solution can be added. If the Brix measurement changes with the addition of the emulsion, the gelatin can be further cooked to a higher Brix. As used herein, the Brix measurement refers to the amount of dissolved solid in a liquid. The emulsion is not cooked prior to infusion.

For a pectin-based product, sugar, corn syrup, gelling agent and water are first combined under heat to form a homogenous phase. After that, the flavor color can be added, then the emulsion can be added. In some embodiments an acid solution is added at last step. If the Brix measurement changes with the addition of the emulsion, the emulsion can be added at the end of the cooking process and gently heated.

The depositing step can include transferring a cooked gummy batch into small molds of various shapes. Starch or silicon molds can be used. Starch molds can be made by filling a tray with corn starch. Afterward, a shape can be impressed into the starch to create the mold. Silicon molds are standard in the industry. Custom silicon molds are available to be created by a few mold makers in any desired shape. The method can include coating the mold in oil prior to depositing to aid the demolding process.

In some cases, the infused gummy base can be poured over a large flat plate and cured as one piece without a mold. After curing, this large piece of gummy can be cut into certain weights and shapes to produce final product.

In the curing/conditioning step, the gummy can take 24-48 hours to set and dehydrate slightly. The variance in time is dependent on starch or silicon molds, the formula, the temperature, and relative humidity of the room they are curing in. Stoving rooms can be used. In general, a temperature of 65-72° F. (e.g., 66° F., 67° F., 68° F., 69° F., 70° F., 71° F., or 72° F.) and relative humidity at 25% or below (e.g., 24,%, 22%, 20%, 18%, 16%, 14%, or 12%) can be optimal conditions. If the room is too hot or dry, a hard skin will form on the outside trapping moisture inside. There are certain pectin gummy formulas where the curing can be complete within 12 hours, sometimes 8 hours, sometimes, 6 hours, or 4 hours or 2 hours.

Demolding can include removing finished gummies from the silicon molds or starch molds.

The demolded product can be coated in a coating material. The coating material can include sugar, wax, sour sanding (e.g., citric acid, 50%/50% citric acid/sugar, ascorbic acid), and/or a combination thereof. The coating can prevent the gummies from sticking together in the packaging; provide protection from moisture; and/or create an attractive and/or glossy appearance. Coating applications can include but are not limited to sanding and oiling. Sanding can refer to coating the gummy with a sugar or a sugar and acid mix. Oiling can refer to coating the gummy in a small amount of oil, such as carnauba wax and/or beeswax in MCT oil.

The gummies can be packaged in bottles, mylar bags, plastic bags, metallic bags and/or the like.

There can be slow and fast-setting pectin types. In some embodiments, a buffering agent such as about 0.1% of sodium citrate, or any buffering agent known in the art, can be added to pectin prior to mixing it with heated sugar and corn syrup to decrease the setting time. Likewise, any acid solution, such as citric acid, can be added after all the other ingredients have been incorporated. The acid can cause the pectin to begin to set, which can also cause the mixing of ingredients added afterwards to take more time.

In large scale production, the longest time cost step is the setting time, which is defined by the time between gummy being deposited into the mold and ready to be demolded and sanded. Usually, this step can take anywhere from 12 hours to 48 hours, depending on the gummy matrix. Gelatin usually takes a shorter time to set than pectin, which usually need >36 hours before it is firm enough to pop out of the mold. However, there is a special pectin-based gummy with a very short setting time. For small scale production, the setting time usually takes less than 1 hour (e.g., 55, 50, 45, 40, 35, 30, 25, 20, 15, or 10 minutes). For large scale production, it usually takes less than 12 hours. The shorter setting time dramatically increases the productivity in terms of how many gummies can be produced in a single shift and also the labor arrangement around the shift. The ingredients and amounts are shown in table below.

TABLE 4

| Section 1 | Weight (g) | Instructions |
|---|---|---|
| Cold Water | 300-400 | a) Cold water is preferred, e.g., under 80 F. |
| Sodium Citrate | 1-5 | b) Add ingredients into water quickly under stir |
| Pectin Slow Set | 15-30 | c) 5:1 ratio of sugar:pectin protects pectin from |
| Sugar | 100-300 | burning |
| | | d) Heat till boil (bubbling), and then heat for 5 more minutes to "activate" pectin |
| | | e) Preferred pectin is from apple peal |
| Section 2 | | |
| Sugar | 300-500 | a) preferred glucose Powder is the special type, |
| Glucose Powder | 200-400 | b) Glucose syrup can be any type |
| Glucose Syrup | 100-150 | c) Warm up this mixture to be ready to be boiled |
| Water | 100-150 | d) When Section 1 is boiled for 4 minutes, start to boil this part |
| | | e) After combing Section 1 and 2, use weight scale to monitor how much water to cook off. |
| | | f) Use target potency as weight target: emulsion mg/TOTAL WEIGHT = final gummy potency |
| Section 3 | | |
| Color | 10-20 | a) All ingredients are pre-weighed |
| Flavor | 0.2-0.5 | b) Place them on cooktop to warm, so they do not cold shot when infused into mixture. |
| *Quillaja* Extract or Gum Acacia Emulsion | 20-60 | |
| Section 4 | | |
| Citric Acid 50% Solution | 10-20 | a) This is for distillate-based gummy, b) for emulsion-based gummy, may need to reduce the amount of citric acid |

In addition to gummies, the invention relates to emulsion-infused condiments, hard candies, lozenges, cough drops, ice pop, chewing gums, ice creams, gusher candies, and/or any other edible products that contain any amount of water. The *Quillaja* extract and gum acacia-based emulsions are most suitable to be infused into these products because these emulsions (1) do not offer too much flavor off-note and (2) they are easy to blend in and they are compatible with the ingredients from the main base food matrix. In contrast, emulsions made by other main emulsifiers shown in the Examples can product a bitter taste, or cause uneven "hot spots" during heat, or are not compatible with the food matrix base. The ratio of those two working emulsions was shown below. They can both be produced by mixing homogenous a water phase (water containing either *Quillaja* Extract or gum acacia) with an oil phase (carrier oil with active agent(s) under a high shear mixer, then the raw emulsion can be feed into ultrasonication or high-pressure homogenizer for 1-5 passes at 10,000-45,000 PSI. In both processing conditions, it can be preferred that the temperature is kept below 50° C.

TABLE 5

| Two main emulsion types to be infused into edible products | Weight (g) | | | | | |
|---|---|---|---|---|---|---|
| | Active agent(s) | Carrier oil | *Quillaja* Extract | Gum Acacia | Stabilizing agent (antioxidant, preservatives and pH modulators) | Water |
| *Quillaja* Extract based emulsion | 1 | 0.5-10 | 0.075-5 | 0 | 0.0-0.5 | 1.7-50 |
| Gum Acacia based emulsion | 1 | 0.5-10 | 0 | 1-22 | 0.0-2 | 3.5-150 |

Condiments

In some embodiments, the edible product can be a condiment. The emulsion can be infused into a condiment base to form the edible product.

The condiment can include but not be limited ketchup, tomato sauce, Vegemite®, lemon juice, narsharab, raita, kasundi, achaar, chutney, aji, pebre, vinegar (e.g., rice vinegar, Chinese vinegar), duck sauce, hoisin sauce, ginger dressing, oyster sauce, plum sauce, *mala* sauce, sweet bean sauce, tauco, XO sauce, yellow soybean paste, shacha sauce, sichuan (or Szechuan) pepper sauce, soy sauce, hot sauce (e.g., Tabasco®, Sriracha®), cornichons, croutons, mayonnaise, pistou, ajika, tkemali, curry, kren, zigeuner sauce, shito, groundnut, fava, melitzanosalata, skordalia, pickle juice, relish, raita, sooth, ouu khatta, kerala pachadi, putnis, alioli, agliata, capuliato, garum, gremolata, pesto, saba, vincotto, salmorglio, krupuk, kecap, palm vinegar, mirin, kombu, karashi, ponzu, shiso, shichimi, dashi, karashi, miso, wasabi, wafu dressing, tare sacue, cheong, jang, jangajji, jeotgal, kimchi, *perilla*, mustard, kaya, adobo, chamoy, mole, pipian, salsa roja, fruit sauce or jam (e.g., apple, cranberry, strawberry), meat sauce or marinade (e.g., steak, barbecue), hummus, peanut butter, agre dulce, atchara, bagoong, khrenovina sauce, aioli, bostongurka, vanilla sauce, aromat, cenovis, nam chim, brown sauce, HP™ sauce, KEEN'S™, mint sauce, salad dressing, relish, mambo sauce, any other condiment, and any combinations thereof.

The emulsion types in Table 5 can be infused into condiments. The active agent can include one or more cannabinoids, terpenes, and/or other nutraceutical hydrophobic compounds. If there is more than one active agent, they can be combined to produce a single emulsion. Alternatively, an individual emulsion with single active agent can be produced, measured, and then infused into the final condiment products to target potency levels.

Many types of carrier oils can be used. Selection of the carrier oil can depend on the nutritional, allergen, and other label requirements of the condiment brand. For example, the carrier oil can include either oil derived from plants (e.g., sunflower oil, olive oil, coconut oil, sesame oil, avocado oil, palm oil, soybean oil, corn oil, peanut oil, canola oil, grape seed oil, corn oil, hazelnut oil, rice bran oil, linseed oil, safflower oil, sesame oil, passion fruit oil, or combinations thereof) or oil derived from animal parts (e.g., lard, butter, cheese, any animal fat, or combinations thereof). The amount of oil can be at least the same as the active agent.

Emulsifiers Vitamin E TPGS, polysorbate series (Tween® 20, Tween® 40, Tween® 45, Tween® 60, Tween® 65, Tween® 80, Tween® 81, and Tween® 85), Polyglycerol (e.g., Polyglyceryl-10 Dipalmitate, Polyglyceryl-10 Oleate, Polyglyceryl-10 Laurate, and Polyglyceryl-10 Caprylate/Caprate), are not preferred due to flavor off notes and/or their negative effect on texture.

The water amount can vary, but is typically present in a higher amount than the total combined weight of active, carrier oil, main-emulsifier, and co-emulsifier. The water amount can depend on the final condiment's target potency.

In some embodiments, the emulsion (or emulsions) can be infused into the condiment at the step where water is introduced into the manufacturing process of the condiment. In other embodiments, the emulsion (or emulsions) can be introduced at the final step when all other ingredients are mixed. Infusion can include stirring agitation for a period of time sufficient for the emulsion to be dispersed homogeneously throughout the condiment.

The three challenges for infusing condiments can include (1) ingredient compatibility, (2) long term potency stability, and (3) flavor impact.

In some embodiments, the emulsion can be tested for ingredient compatibility between the emulsion and condiment. A sample of the test product can be kept at higher temperature to accelerate any undesirable effects such as a separation of layers, sedimentation, or "O-ring formation". An "O-ring" is a description for a light-colored ring that can appear on the top of the solution when a solution is placed in a container like a test tube. Formation of an O-ring can be a sign of instability: when emulsion droplets merge and become bigger, if the emulsion oil phase density is lower than water phase, it may float to the top of the solution and form a ring that resembles an O-ring seal. In some embodiments, the ingredients are compatible if no undesirable effects are observed after 4 months at 40° C. or 12 months at room temperature.

The condiment can be sealed inside a disposable bag for one time use, such that the bag can prevent light and oxygen exposure to the product to improve stability. In some embodiments, antioxidants can be used improve stability. Antioxidants can include EDTA, water-soluble rosemary extract, ascorbic acid, Brew Shield®, Structan®, and/or the like.

Some embodiments of the invention can include testing and adjusting the flavor. As an example, the inventor has found that polysorbate and vitamin E TPGS based emulsions are not ideal for ketchup and hot sauce, due to the bitter taste that does not align well with the original products' flavor profile.

Hard Candies, Lozenges, Cough Drops, Etc.

The invention can also include infused cough drops, lozenges, lollipops, hard candies, and/or the like. Such forms can offer benefits such as discreet use, ease of use, and metered/predictable dosing.

Embodiments of the invention can relate to making a cough drop, lozenge, lollipop, hard candy, and/or the like by adding the emulsion late in the production process to avoid degradation by high heat and evaporate moisture from the product. The emulsion can be added as late as possible in the candy making process as the water from the emulsion needs to be evaporated fully in order for the candy to set properly and be devoid of cold flow and graining.

The emulsifier can be an emulsifier that does not negatively impact the flavor of the product. Through experiments, the inventor has confirmed that such emulsifiers can include gum acacia, *Quillaja* extract, Tween® 20, Tween® 60, Tween® 80, and Polyglyceryl-10 Dipalmitate.

The product can have homogeneity, accurate potency targeting, and multi-active ratio dosing. Multi-active closing can include combining different active compounds from cannabinoids or terpenes together to achieve an entourage effect. For example, a 3:5 THC:CBN ratio can help with sleep, a 1:1 CBD:CBG ratio can help with pain relief, a 5:1 CBD:THC ratio can be used to deliver a balanced mindset.

Ice Pop

In some embodiments, the edible product is an ice pop (e.g., Popsicle®) or similar product. Ice pops can include a liquid flavor and can be frozen prior to consumption. The emulsion composition can be added to the sweetener (e.g., *stevia*, honey, sugar, and the like) and liquid base. The liquid base can include water, juice, dairy, soy milk, almond milk, hemp milk, coconut milk, coconut water, and the like. The liquid base can also include flavors, fruit juices, coatings, or toppings (e.g., chocolate or nuts), and fillers or mix-in ingredients (e.g., chocolate, nuts, nut butter, cream). The emulsion composition can be added as the last step into the already formulated ice pop base, where constant stirring can help homogenize the emulsion throughout the batch to reach potency homogeneity. Since the ice pops are in liquid form at room temperature and get frozen before consumption, the ingredients' physical compatibility can be an important feature to make sure there is no layer separation, precipitation or ingredient falling apart prior to the low temperature treatment. In some embodiments, the main emulsifier type can be gum acacia, *Quillaja* extract, Tween® 20, Tween® 60, Tween® 80, and Polyglyceryl-10 Dipalmitate, and/or the like. The final selection can depend on flavor impact and its appearance (clear or cloudy).

Ice Cream/Frozen Yogurt

In some embodiments, the edible product is ice cream or a similar product (e.g., gelato, frozen yogurt). In those products, there is an existing base emulsifier that stabilizes the fat with aqueous ingredients, such as polysorbate. *Quillaja* extract or gum acacia emulsion can be compatible emulsions for ice cream or a similar product.

The emulsion can be added into the base ice cream or yogurt mixture (or similar product) at the very last step, where other ingredients are already mixed well into one homogenous phase.

The product can also be a frozen solid ice cream beans produced under −80° C. liquid nitrogen. The emulsion composition can be mixed into an ice cream aqueous mixture (base) prior to the cooling process. The emulsion composition used can depend on texture change (physical compatibility of the ice cream ingredients with emulsifier) and the final flavor and mouth feel.

Chewing Gum

In some embodiments, the edible product is a sugar or sugar-free chewing gum or similar product such as a quick-dissolving soft chew (e.g.: Mentos® or Skittles®). The emulsion composition can be infused directly into the gum base, chewing gum stick or slab, candy layer, pellet gum liquid core, pellet-gum powder core, or pellet-gum coating. The chewing gum can include is not limited to a minty, fruity, spicy, or savory flavor. The product can include a coating (e.g., sweet or sour) or multiple layers with candy as one of the layers. The product can include a coating applied by spray or candy panning. The product can include a coloring substance.

General sugar-free chewing gum making process: sugar alcohols can be blended together in a mixer (e.g., a double arm Sigma blade mixer) or kettle that has been preheated to approximately 100° F. then the gum base is added which has been melted to 80-195° C. and mixed. Other ingredients can be then added such as emulsifiers and plasticizers are added and mixed for a few minutes. Then flavors and coolers can be added (mostly liquid, some dry) and mixed for a few minutes, then a dry powder blend consisting of food acids, high intensity or natural sweeteners and some spray-dried flavors can be added and mixed. Then the gum can be flattened into sheets to a specific height and cut into pieces, formed into pellets or center filled pellets for coating using equipment such as rope sizers and chain dies to cut the rope into pieces.

The emulsion can be added at the beginning, middle or end of the manufacturing process. Depending on the processing temperature, it can be added at the end of the process to prevent excessive heating of the cannabinoids during the gum base melting step. In some embodiments, it is added to a coating or powdered center fill. In other embodiments, it is added to the gum base or gum core itself. In some embodiments, the emulsion can be added to the candy layer, liquid center fill, powder center fill, and/or to coating.

Chewy Candy with Juice Center

In some embodiments, the emulsion-infused product is a candy such as a "Gusher™" candy. A gusher is a product that has a hard shell (e.g., chocolate or sugar) surrounding a liquid core. The liquid core can include ingredients, such as but not limited to sugar, alcohol, and the like. A *Cannabis*-infused gusher has *Cannabis* emulsion infused into the liquid core (e.g., a delicious chocolate and then a flavorful *Cannabis* emulsion with quick onset), so the consumer can have an enjoyable experience.

A gusher may only have about 0.3 mL for the empty volume inside. To make the emulsion flavor appealing to a consumer, it may need 0.2 mL reserved for a flavor agent or agents. In such an embodiment, the volume for the emulsion would be only 0.1 mL. If each gusher is targeting 15 mg of cannabinoid, then the starting potency would be equal or higher than 150 mg/mL (15 mg/0.1 mL). Since the emulsion density is usually around 1 g/mL, the starting emulsion potency could be equal or higher than 150 mg/g.

The emulsion used in this application can have the following ingredients:

TABLE 6

Emulsion for infusion into a gusher candy

| Ingredients | Mass (g) |
|---|---|
| Active Agent | 1 |
| Carrier oil | 0.5-10 |
| Quillaja Extract or Gum Acacia | 0.075-2 |
| Preservative/Stabilizer | 0-2 |
| Water | 3-10 |

Some embodiments of the invention relate to a method of making a "gusher" candy. A gusher candy can be defined as a candy that has a sugary shell holding up a liquid core that can be released once the sugary shell melts in the mouth. In some embodiments, the invention relates to a Cannabis-infused gusher where the Cannabis can either be incorporated into the sugary shell, for example, as a chocolate or the inner liquid. Usually, the inner liquid is placed on the outside shell as a wax or solid at low temperature, and the layered material gets wrapped up and chopped into individual candy. When returned to room temperature, the wax or solid internal material melts to become liquid. In the case of applying Cannabis emulsions, the emulsion can first get mixed with another flavoring agent first and follow the similar process to get this mixture frozen at −5° C. to 0° C. for over 5-24 hours (e.g., 5.1, 5.5, 10, 15, 20, 24, or 25 hours). After taking out this material from the freezer and letting it melt into a state where it is not too hard to reshape, it can be placed onto the sugary base. There is usually 1-3 hours (e.g., 1, 1.2, 1.4, 1.6, 1.8, 2, 2.2, 2.4, 2.6, 2.8, or 3 hours) to allow this placing to happen if the environmental temperature can be controlled below 10-15° C. (e.g., 5, 6, 7, 8, 9, 10, 11, 12, 13, 14, or 15° C.). After the cannabinoid emulsion liquid mixture is placed, wrapped with sugary base, and cut into individual pieces, the following steps can be similar to produce regular gusher.

High Fat Foods

In some embodiments, the edible product can be any food that has fat and/or oil as the dominant ingredient(s). Such products can include but are not limited to chocolate, cookies, cakes, popcorns, biscuits, cakes, pastries, cream, sour cream, cheese, savory snacks, and the like.

A microemulsion can be used. The microemulsion can be formed with mild agitation such as under heat. In some embodiments, the temperature is kept below 50° C. In some embodiments, mild agitation can be achieved by an overhead stir or a high-shear mixer running below 8,000 rpm. The emulsifier can be polyethylene glycol (PEG), polysorbate, vitamin TPGS, and the like.

The table below provides an embodiment of a microemulsion. The main emulsifier can come from synthetic category such as polysorbate 20, polysorbate 60, polysorbate 80, Vitamin E TPGS; the main emulsifier can also come from the natural category such as Quillaja extract.

TABLE 7

| Ingredient | Weight % |
|---|---|
| Active Agent (e.g., cannabinoid) | 10-20 |
| Carrier Oil | 5-30 |
| Glyceryl Caprylate | 10-20 |
| Main Emulsifier | 30-75 |

The microemulsion can be added into high-fat edible products such as chocolates, cookies, cakes, popcorns, biscuits, cakes, pastries, creams, sour creams, cheeses, savory snacks, and the like. The emulsion addition step can differ depending on the product type. In some embodiments, the emulsion is added with other liquid oil-based ingredients into the product base during the mixing step. In some embodiments, a higher temperature in range of 50-95° C. can be used to ensure thorough mixing between ingredients. Also, since there is no water to evaporate off, in order to adjust the total weight and thus targeting the potency, the initial weights of the ingredients need to be carefully calculated.

Compared to standard oil-based products, where a cannabinoid takes a very long time to be transferred by natural emulsifiers in the body (e.g., bile salt or lecithin), a microemulsion can be absorbed into epithelial cells within the small intestine. Thus, a microemulsion product can provide a faster onset with higher bioavailability. Other hydrophobic compounds that can be infused into high-fat edible products can include, but are not limited to, vitamin E, vitamin B12, vitamin A, vitamin D, vitamin B, Omega 3, astaxanthin, fish oil, MCT oil, coconut oil, palm oil, eicosapentaenoic acid (EPA), docosahexaenoic acid (DHA), essential oils such as Lemon oil, orange oil, peppermint oil, ylang-ylang oil, lemon grass oil, tea tree oil, rosemary oil, Australian sandalwood oil, grapefruit oil, frankincense oil, cedarwood oil, patchouli oil, cinnamon bark oil, bergamot oil, chamomile oil, lemon eucalyptus oil, ginger oil, key lime oil, vanilla oil, and/or clove oil.

EXAMPLES

Example 1

A CBD isolate- (distillate-) infused gummy and a CBD Quillaja extract-(emulsion-) infused gummy, both targeting 1 mg/g target, were produced and tested. The CBD isolate was first dissolved into MCT oil and then added into the gelatin base at 250° F. under constant stirring.

Figure 2:
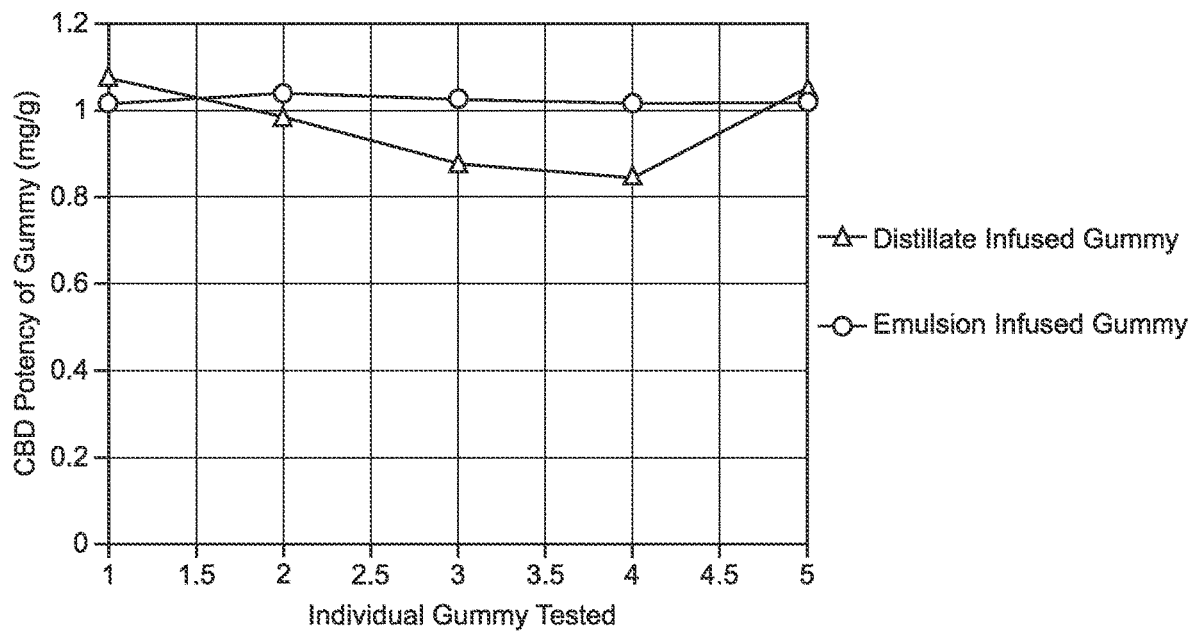
FIG. 2 shows results from experiments comparing potency in emulsion-infused gummies versus distillate-infused gummies.

When individual gummies from the sample batch were tested for CBD potency, the distillate-infused gummies showed a larger discrepancy and higher standard deviation than the emulsion infused gummies (See FIG. 2). This may explain why consumers report inconsistent experiences with distillate-infused gummies. When distillate-infused gummies are being tested for full compliance prior to their market release, 5-10 gummies are usually taken as one sample and combined together for potency quantification. This sampling method can make the average closer to the target potency value to pass the test, but the end product may contain uneven potency distribution.

In another experiment, a 5 g gummy mold was used to make 3 types of gelatin gummies targeting 3 different potencies: 2 mg/g (1.0 mg/5 g), 3 mg/g (15 mg/5 g), and 5 mg/g (25 mg/5 g). The results are shown in the table below. For all three pilot tests, the potency for the emulsion infused gummies was within 3% of the target.

TABLE 8

| Target CBD per gummy (mg) | Gummy weight (g) | Target Potency (mg/g) | Tested Potency (mg/g) | Difference % |
|---|---|---|---|---|
| 10 | 5 | 2 | 1.97 | −1.5% |
| 15 | 5 | 3 | 3.07 | +2.3% |
| 25 | 5 | 5 | 5.06 | +1.2% |

Example 2

Three emulsions were produced using *Quillaja* extract as the emulsifier. The first emulsion had CBD as the active agent, the second emulsion had CBG as the active agent, and the third emulsion had myrcene as the active agent. The active agents were all targeted around 60 mg/g. During the gummy production process, specific amounts of each emulsion were mixed into the gummy base, targeting CBD:CBG:myrcene=3:1:0.2. Gummies were produced and tested with HPLC-DAD for cannabinoids profile and direct inject GC-FID for terpene profile, the end result proved *Quillaja* extract emulsion can hit the target ratios very accurately.

TABLE 9

3:1:0.2 as CBD:CBG:Myrcene ratio gummy infused by three emulsions

| Cannabinoids within the Gummy | Targeted Ratio | Tested Potency |
|---|---|---|
| CBD:CBG:Myrcene | 3:1:0.2 | 1.51:0.51:0.11 = 2.96:1:0.21 |

This shows that the *Quillaja* extract emulsion can allow accurate design and loading of gummies with multiple cannabinoids. It was surprising to find that *Quillaja* extract as the emulsion droplet shell protected the myrcene from evaporating and losing potency during the high heat process.

Example 3

Six types of emulsions (shown in the table below) were tested in both the pectin-based and gelatin-based gummy to evaluate ease of production, compatibility with the base, impact on texture and flavor and experience.

TABLE 10

Six major types of emulsions that were tested in gummy infusion

| Emulsifier Type | Emulsion droplet size (nm) | Emulsion taste | Starting potency (mg/g) | Viscosity (cP) | Density (g/mL) |
|---|---|---|---|---|---|
| Cyclodextrin | 25 | Neutral | 10 | 1.20 | 1.01 |
| Vitamin E TPGS | 35 | Slightly bitter | 30 | 1.37 | 1.04 |
| Polysorbate 60 | 50 | Slightly bitter | 30 | 1.25 | 1.02 |
| Polyglycerol Ester of Fatty Acid | 120 | Neutral | 20 | 2.56 | 1.06 |
| Quillaja Extract | 200 | Neutral | 60 | 1.27 | 1.07 |
| Gum Acacia | 500 | Neutral | 40 | 1.47 | 1.11 |

An experiment was performed to evaluate the feasibility of using different emulsion types in gummy infusion. A large portion of the gelatin and sugar base was prepared at 240° F. After the base of sugar plus pectin or gelatin is homogenized, it is divided into seven portions, which all maintained a consistent temperature. Following this, six different emulsion types with THC as the active were added to target 5 mg THC/5 g gummy (1 mg/g potency). The goal was to test the original flavor, appearance, and texture created by introducing emulsion into the gummy, therefore no flavor agents or colors were added. The seventh portion was used as a control sample and remained uninfused. All seven samples were deposited, cured, and demolded by the same condition and timing. The following criteria were used to evaluate emulsion compatibility with the gelatin gummy base: ease of production, compatibility of emulsion with gelatin base, Brix, texture, appearance, flavor, and experience.

Example 4

Six types of emulsions (shown in the Table below) were tested for use in a gelatin gummy.

TABLE 11

Gummy evaluation based on different emulsion infusion

| Emulsifier Type | Production Process | Texture | Flavor | Onset (minutes) |
|---|---|---|---|---|
| Cyclodextrin | Lower Brix, needs long time heating | In desired range | Slightly bitter | 20 |
| Vitamin E TPGS | Workable | Soft | Strong bitter | 10 |
| Polysorbate 60 | Workable | Soft | Strong bitter | 15 |
| Polyglycerol Ester of Fatty Acid | Causes more sugar burning | Rigid | Slightly bitter | 20 |
| Quillaja Extract | Workable | In desired range | Neutral | 10 |
| Gum Acacia | Workable | In acceptable range | Neutral | 15 |

The table above summarizes the gummy properties when infused by the different emulsions. The evaluation is done based on the texture, flavor, and experience of the finished gummy.

It would be expected that all emulsions would work in terms of delivering cannabinoids into the gummy system since they are all oil-in-water types and thus can be easily infused. Surprisingly, only emulsion produced with *Quillaja* extract and gum acacia showed superior results in a finished gummy product. Vitamin E TPGS and Polysorbate 60 based emulsion offered a strong bitter gummy taste, which may have come from their own emulsion flavor. Also, when combined with the gelatin base, they made the matrix less viscous and softened the texture, which made the gelatin gummy less chewy. Cyclodextrin-based emulsion dramatically lowered the Brix of the gummy system, which required longer heating time (>20 minutes) to evaporate the water and adjust the Brix back. This step not only caused damage to the gummy ingredient but also caused potency loss in the cannabinoids.

Gummies infused by polyglycerol ester of fatty acid emulsion offered a rigid texture, possibly due to its higher viscosity.

The results suggested that the emulsion made with *Quillaja* extract or gum acacia are most ideal to be used in gummies.

Example 5

Emulsions A-L in the following Table were made and tested for use in gelatin gummies with no additional bitter blocker or flavor agent.

All the emulsions were produced by combining the water phase with *Quillaja* extract and oil phase with cannabinoids and carrier oil before processing through either a high shear mixer or sonication. Afterward, the raw emulsion is introduced through a high-pressure homogenizer, microfluidizer device, or continued sonication. The pressure for microfluidizer can be 10,000 PSI to 40,000 PSI and it can go through it by 1-5 passes. The average droplet size ranged from 110 nm to 450 nm with a PDI from 0.01-0.4. The *Quillaja* extract emulsion had at least a 12-month shelf life against gravity layer separation, potency loss, microbial growth, pH, flavor, and density change.

TABLE 12

| Emulsion Code | Cannabinoid Isolate (g) | Carrier Oil (g) | *Quillaja* Extract | Water (g) | Total Weight (g) | Potency (mg/g) |
|---|---|---|---|---|---|---|
| A | 1 | 1 | 0.28 | 0.6 | 4 | 250 |
| B | 1 | 2 | 0.42 | 0.9 | 6 | 167 |
| C | 1 | 3 | 0.56 | 1.2 | 8 | 125 |
| D | 1 | 4 | 0.7 | 1.5 | 10 | 100 |
| E | 1 | 5 | 0.84 | 1.8 | 12 | 83 |
| F | 1 | 5 | 0.36 | 9 | 16.8 | 60 |
| G | 1 | 5 | 0.24 | 4.2 | 11.4 | 88 |
| H | 1 | 4 | 0.7 | 6 | 14.5 | 69 |
| I | 1 | 4 | 0.7 | 10 | 18.5 | 54 |
| J | 1 | 4 | 0.7 | 15 | 23.5 | 43 |
| K | 1 | 4 | 0.25 | 6.7 | 11.95 | 84 |
| L | 1 | 1.5 | 0.125 | 6.7 | 10 | 100 |

A pectin-based gummy was produced using the same recipe and process, but interchanging the emulsion that was infused and the final gummy potency was targeted at 2 mg/g. While infusing gummies with emulsions A-D, the *Quillaja* extract was kept at the same ratio and the carrier oil amount was increased from 1 to 4 times the cannabinoid. Unexpectedly, the gummy flavor changed from less bitter to more bitter.

When comparing infused gummy samples between E-G, keeping the carrier oil ratio same but decreasing the *Quillaja* extract amount, the bitterness in the gummy also decreased. Unexpectedly, from E-G, when decreasing the *Quillaja* extract: cannabinoid ratio, the overall experience of the gummy changed: onset time grew longer and the overall intensity was lower. This suggests that by controlling the ratio of *Quillaja* extract, different consuming experiences can be achieved.

For example, if the objective of the gummy product is to have a quick onset and an intense experience, then the ratio of *Quillaja* extract to cannabinoid should be higher. If the objective of another gummy product is to have mild intensity and to encourage consumers to consume multiple gummies throughout the experience session, then the *Quillaja* extract to cannabinoid ratio should be lower.

If the ingredients in gummy samples infused with emulsions D, H, I, and J were kept the same but the water amount was increased, the emulsion potency and viscosity will decrease. In order to maintain potency, more emulsion weight needs to be added. This can change the texture of the gummies and as well as the time needed to balance the Brix to the ideal level. The longer heating time also contributes to decreased cannabinoid potency.

Emulsions K and L have a lower ratio of *Quillaja* extract to total oil load. Specifically, the *Quillaja* extract accounts for around 0.05 the total amount of carrier oil and cannabinoids. This formula resulted in a less bitter version of the infused product.

Carrier oil amount is also a key factor for total absorption of the cannabinoids. The inventor has tried MCT, LCT, mineral oil and flavor oil such as orange oil as the carrier oil, surprisingly, MCT oil offers the highest perceived intoxication feeling, followed by LCT. Mineral oil and flavor oil can not be digested so that they do not help with formation of mixed micelle in the small intestine. However, MCT will be altered into fatty acid and monoglyceride which can be used as raw ingredients for the formation of mixed micelle, which is the main vehicle that cannabinoids can be absorbed. When using the MCT oil as carrier, Emulsions D-K provided higher perceived intoxication feeling compared to Emulsions A-C likely due to the amount of carrier oil present.

Example 6

Optify™ (from FONA International), TruClear™ (from Tastes Natural™) Flavor Taste Modifier (from Biogenic Foods®) were tested as bitter blockers. By adding the same amount (1%) of each bitter blocker into the gummy base, surprisingly, only Optify™ reduced the bitterness and stringiness coming from the *Cannabis* emulsion. Optify™ reduced the overall sharpness of the gummy flavor and bitterness from the emulsion.

Also, surprisingly, not all flavors worked well with the *Cannabis* emulsion. After many combination trials, it was discovered that the following individual flavors work best when used along with emulsion and Optify™: berries (blueberry, raspberry, or mixed berry), mint, tropical, passionfruit, matcha tea, guava, lavender, and mango. As for flavor combinations, blackberry-mint, basil-ginger, and mango-lime worked well.

The following flavors were found to be less desirable with the *Quillaja* extract *Cannabis* emulsion: lemon, cinnamon, and strawberry.

Example 7

This example provides specific steps for making a gelatin gummy.
1. Combine gelatin and cold water, set aside for 10 minutes.
2. Combine sugar, water, and corn syrup, begin to heat while stirring with a heat stable spatula. Mixture should reach a minimum of 180° F.
3. Once mixture reaches 180° F., Add Part 1 with slow mixing to the Part 2 syrup and until completely dissolved. Mix by hand very slowly to avoid incorporation of air. Slowly heat mixture to −230° F.

4. Using a refractometer, measure Brix to target at 78-81. If too high, add water and remeasure. If too low continue to cook a little longer and remeasure until target is reached. Record final value.
5. Remove from Heat. Cool to 215-220° F. then add THC emulsion, mix gently for 1-2 minutes until the syrup looks homogenous.
6. Using a refractometer, measure Brix and record value.
7. Add Part 4, mix gently for 3-5 minutes depositing batch within 30 minutes. The acid will reduce the gelling strength if held too long, especially at higher temperature.
8. Pour gummy mixture into a heated, dry depositing funnel. Deposit the blend into silicon molds as soon as possible. Fill about ⅘ of the way to the top.
9. Demold after 18-24 hours. If backs of gummies are overly dry (coating doesn't stick), then using coat gloved hands with water, lightly run the hand over the backs of the gummies while in the mold. (or steam the backs of the gummies while in the tray). Pop from molds and coat gummies in sour sanding by rolling them in the sanding mixture. Let cure on wax paper for an additional 24 hours.

TABLE 13

| STEP | INGREDIENT | PERCENTAGE | GRAMS |
|---|---|---|---|
| 1 | Water | 12.76 | 127.59 |
|   | Pork Gelatin (250 Bloom) | 6.2 | 62 |
| 2 | Water | 9.07 | 90.7 |
|   | Corn Syrup 42 DE | 41.019 | 410.17 |
|   | Sucrose (Table Sugar) | 25.32 | 253.19 |
| 3 | THC: *Quillaja* extract emulsion (97.78 mg/mL) | 2.126 | 21.26 |
| 4 | Optify ™ Bitter Masker Flavor 936.3680U | 1 | 10 |
|   | Mango Lime Flavor 870.2313U | 1 | 10 |
|   | Green Solution | 0.01 | 0.1 |
|   | Citric Acid Solution (50%) | 1.5 | 15 |
| TOTAL |  | 100 | 1000 |

The following provides an example procedure for producing a gelatin gummy on a smaller scale.

Collect equipment and set aside all ingredients for measurement: equipment=small, medium, and large stainless-steel pots, two induction burners, scale, refractometer, thermometer, three rubber spatulas, stainless steel ladle, whisk, sheet tray, [warm] silicone molds, pastry scraper, extra distilled water (for Brix correction).

Ingredients are categorized into: Kit 1=sucrose and distilled water; Kit 2=gelatin; Kit 3=corn syrup and coloring; Kit 4=*Cannabis* active ingredient, citric acid, flavoring, and bitter blocker.

Thoroughly mix sucrose and water (kit 1) into a medium sized pot until sucrose is at least 85% dissolved. Then mix kit 2 into kit I; set aside and allow gelatin to bloom for 10 minutes. Once fully bloomed, heat the mixture (let's call it kit 2 from now on) slowly to 180° F. and hold at this temperature; do not go below 180° F. Carefully measure the corn syrup amount in kit 3 into a large stainless-steel pot using the ladle and a rubber spatula; add coloring. Place the pot with kit 3 on the other induction burner. Bring kit 3 up to 180° F. and hold at this temperature; do not go below 180° F. Pour, while whisking, kit 2 into kit 3. Using a small, white, disposable measuring tray and the refractometer, check the Brix level of the mixture. Place silicone molds onto a sheet tray directly next to the induction burners. 78% Brix is the goal for this step so if it is too high, bring it down with the extra distilled water; if it is too low, allow the mixture to cook longer with periodic checks with the refractometer. Whisk kit 4 into the mixture once desired Brix has been achieved. Check Brix again; 78-81% Brix is the goal for this step. Once the final desired Brix has been achieved, pour entire contents of the gummy mix into the silicone molds. Working very quickly with the pastry scraper, push and move the gummy mixture around the silicone molds to fill gaps as much as possible to create a smooth surface. Place sheet tray and silicone molds filled with gummy mix on the bun rack/speed rack and allow to set for 25 minutes in a room no warmer than 72° F. After 25 minutes, place the gummies into a refrigerator. The gummies, while setting to their molds, should be stored in this fridge or in a room no warmer than 70° F. for at least 24 hours.

Example 8

This example provides exemplary specific steps for making a pectin gummy.
1. Dry blend pectin, sugar, and sodium citrate.
2. Add dry blend to water and stir continuously, heat to 185-195° F.; do not let drop below 185° F. Add 175 g more water than in the 100% formula, as it will cook off: ~175 g for a 1000 g batch size.
3. Mix for ~10 minutes to ensure complete dissolution (it will look like a syrup).
4. Combine the remaining sugar and the corn syrup (induction pan or top pan of double boiler). Mix and bring to 185° F. (it will look like a syrup).
   a. Option 1: If using induction pan on induction cooktop: Gradually add pectin solution (Part 1) to Part 2, making sure the mixture does not drop below 185° F. Mix gently for 1-2 minutes until the syrup looks homogenous. Slowly increase and maintain a 212-215° F. temperature while stirring. Mixture can go as high as 230° F. if additional water needs to be driven off.
   b. Option 2: If using the double boiler method: Gradually add pectin solution (Part 1) to Part 2 on top pan of double boiler, making sure the mixture does not drop below 185° F. Mix gently for 1-2 minutes until the syrup looks homogenous. Slowly increase and maintain a 212-215° F. temperature while stirring. When approaching target Brix, transfer the top pan to the induction cooktop to slowly drive off water until Brix is ~74.0. Mixture can go as high as 230° F. Stir consistently and keep mixture on the cooktop sparingly to avoid burning. It is okay to remove the top pan from the cooktop.
5. Using a refractometer, measure Brix to target at 74. If too low, continue to cook a little longer. Once appropriate Brix is reached, record value. If Brix is too high, may need to re-do the batch.
6. While at the 215-230° F. range, add THC emulsion and mix gently for 1-2 minutes until the syrup looks homogenous. Maintain this temperature until you transfer to the depositing funnel.
7. The addition of emulsion volume will likely drop the Brix 1-2 units. Using a refractometer, measure the Brix and record value (aim for 74-76).
8. Add citric acid solution.
9. Briefly mix the solution to ensure full incorporation of the citric acid.

10. Pour gummy mixture into a heated, dry depositing funnel. Deposit the blend into silicon molds immediately. Fill about ⅘ of the way to the top.
11. Demold after 24-36 hours. Pop from molds and coat gummies. Using an airbrush, coat 1 side of the gummies in MCT Let it cure on wax paper for a minimum of 6 hours. Flip and coat the other side and cure for an additional 6 hours.

TABLE 14

| STEP | INGREDIENT | PERCENTAGE | GRAMS |
|---|---|---|---|
| 1 | Water | 12.74 | 175.00 |
|  | Pectin CF 130 B | 1.54 | 0.00 |
|  | Sodium Citrate | 0.10 | 0.00 |
|  | Sucrose (Table Sugar) | 5.00 | 0.00 |
| 2 | Sucrose (Table Sugar) | 25.42 | 0.00 |
|  | Corn Syrup - 62DE | 51.19 | 0.00 |
| 3 | THC: *Quillaja* extract based emulsion (69.39 mg/mL) | 2.996 | 0.00 |
| 4 | Citric Acid Solution (50%) | 1.02 | 0.00 |
|  | TOTAL | 100.00 | 1000.00 |

The following provides an example protocol for preparing a pectin gummy on a smaller scale:

First, collect equipment and set aside all ingredients for measurement: equipment including small, medium, and large stainless-steel pots, two induction burners, scale, refractometer, thermometer, three rubber spatulas, stainless steel ladle, whisk, sheet tray, warmed up silicone molds, pastry scraper, extra distilled water for Brix correction.

Second, prepare multiple kits as ingredients, Kit 1 sucrose, sodium citrate, and pectin; Kit 2=distilled water; Kit 3=corn syrup and coloring; Kit 4=*Cannabis* active ingredient, citric acid, flavoring, and bitter blocker.

Carefully place silicone molds into the incubator/oven/warm space, then thoroughly combine the contents of kit 1 as a dry mixture into a small pot. Slowly whisk (to avoid clumping) kit 1 into kit 2 in a medium sized pot. Place the now combined mix (kit 2) onto an induction burner; put a thermometer in the mix to monitor temperature. Bring kit 2 up to 180° F. (whisking frequently to avoid sticking and boil-over) until it looks like a pale syrup then hold at this temperature; do not go below 1.80° F. Carefully measure the corn syrup amount in kit 3 into a large stainless-steel pot using the ladle and a rubber spatula; add coloring. Place the pot with kit 3 on the other induction burner. Bring kit 3 up to 180° F. and hold at this temperature; do not go below 180° F. Pour, while whisking, kit 2 into kit 3. Using a small, white, disposable measuring tray and the refractometer. Check the Brix level of the mixture. Remove silicone molds from the incubator/oven/warm space and place on a sheet tray directly next to the induction burners. 75% Brix is the goal for this step so if it is too high, bring it down with the extra distilled water; if it is too low, allow the mixture to cook longer with periodic checks with the refractometer. Whisk kit 4 into the mixture once desired Brix has been achieved. Check Brix again; 75-78% Brix is the goal for this step. Once the final desired Brix has been achieved, pour entire contents of jelly mix into the [warm] silicone molds. Working very quickly with the pastry scraper, push and move the jelly mixture around the silicone molds to fill gaps as much as possible to create a smooth surface. Place sheet tray silicone molds filled with jelly mix on the bun rack/speed rack and allow to set for at least 24 hours.

Sometimes, pectin and gelatin can be mixed together to achieve certain level of texture firmness. The ratio between pectin and gelatin can be 50%:50%, 40%:60%, 30%:70%, 20%:80%, 10%:90%. The emulsion infusion method also works for this type of mixture-based gummy.

Example 9

This example provides further information related to making emulsion-infused gummies.

There is a relation between batch size and yield recovery. Smaller batch sizes tend to yield less recovery of the total ingredients in the final gummy batch. There will always be some loss of the batch size due water cooking off. This is particularly apparent for batches smaller than 1000 g.

Testing was done and reported as follows:

A 250 g weighed batch had an output weight (final gummy) of 157.5 g, indicating 63% of the batch was recovered.

A 500 g weighed batch had an output weight of 400 g, indicating that 80% of the batch was recovered.

A 1000 g weighed batch had an output weight of 860 g, indicating that 86% of the batch was recovered.

Example 10

A blind consumer study with 41 participants was performed to evaluate the onset times of the gummies. Each participant consumed THC distillate-infused gummy, and on a separate occasion, consumed a THC emulsion-infused gummy without knowledge of the type of gummy being ingested. The two gummies had the same potency. The subjects were asked to consume each gummy type with an empty stomach and preferably around 4:00 PM. The consumers were asked to evaluate the texture, flavor, and onset time of the gummies.

The majority of participants reported feeling the effects from the emulsion-infused gummies less than 30 minutes after consumption. The average onset time was approximately 15 minutes faster compared to the distillate gummies. 85% of the participants felt the onset of the emulsion gummy within 30 minutes and only 18% of the participants felt the onset of the distillate gummy within 30 minutes; 65% of the participants felt the onset of the emulsion gummy within 20 minutes and only 8% of participants felt the onset of the distillate gummy within 20 minutes; and 50% of the participants felt the onset of emulsion gummy within 10 minutes, while only 4% felt the onset of distillate gummy in that time frame. The results show that the emulsion-infused gummy has a faster onset.

Food consumption can have big impact on the onset. Initial onset can be less than 15 minutes, or 10 minutes or 5 minutes with fasted condition. However, with fed condition, the onset can be 20 minutes, 30 minutes, 40 minutes or longer, depending on the type and amount of food consumed.

Example 11

A pharmacokinetic (PK) study of the gummies was conducted to compare *Quillaja* extract based emulsion infused gummy with distillate-infused gummy. The study was conducted by a Federal Drug Administration/Drug Enforcement Administration licensed lab called Emery Pharma®, located in Alameda, Calif. The sample extraction method was developed by Emery Pharma® to extract cannabinoids from blood plasma samples.

THC was used as the active in the PK study and the THC distillate is of >85% purity, as tested by Emery Pharma®. The *Quillaja* extract based THC emulsion was tested by a third-party lab, which indicates the amount of sample intake at study. Volunteers with a known history of CBD and/or THC intake in the previous month were recruited by Vertosa, Inc. Volunteers underwent blood collection 15 minutes before and 5, 10, 15, 30, 45, 60, 90, 120, 180, 270, 360, and 450 minutes after formulation intake. Additionally, volunteers filled out questionnaires before, during, and after the study. The questionnaires asked volunteers about CBD and/or THC intake in the prior days. Quality of life measurements were recorded during the study.

The collected blood samples were immediately processed for generating plasma, which was subsequently aliquoted in 200-500 μL aliquots and stored in −80° C. When ready for analysis, the plasma samples were thawed at room temperature and processed for LC-MS/MS analysis of CBD, THC, 11-OH-THC, and 11-COOH-THC content.

At each sampling time point, approximately 5 mL of blood was withdrawn.

Subjects were assessed for blood pressure, heart rate, body temperature, any gastrointestinal issues, any feelings of intoxication or "high", and any other feelings or sensations.

Inclusion criteria for volunteers were as follows: males and females, ages 18 to 65 years, intermittent or habitual users of recreational cannabinoids without adverse health outcomes and being able and willing to provide consent.

Exclusion criteria for volunteers were as follows: poorly controlled diabetes mellitus (hemoglobin A1c>8.0% for more than 1 year); obesity and/or hypertension; vulnerable populations, including incarceration status; anticipation of pregnancy during the study; unable to give informed consent; pregnancy, lactation, or child-bearing age without birth control devices; illicit drug abuse or dependence to drugs; any history of psychiatric treatment; concurrent treatment in alcohol or drug detox programs; suspected or exposed to hepatitis and/or HIV; known history of liver and kidney malfunction; and serious illness likely to cause death within the next 5 years.

This was a single center study designed to assess the bioavailability and PK of THC in plasma of healthy volunteers. The goal of this study was to determine the effects of oral gummy formulations on PK of THC in plasma using an oral formulation containing:

1) a pectin gummy infused with 15 mg THC distillate under fast condition.
2) a pectin gummy infused with 15 mg Organic 1 emulsion under fast condition.

The study was conducted over three days. For fasted conditions, subjects remained in a fasted state for 8 hours prior to arrival and were not allowed to use caffeinated products. Upon arrival, volunteers were directed to the appropriate locations and continued to abstain from food until 1 hour after ingesting the gummy formulation. Approximately 5 mL of blood was withdrawn from each subject as the 'control'. At each pre-designated timepoint, each volunteer ingested the oral THC formulation containing 15 mg of THC (active ingredient). For each volunteer, approximately 5 mL of blood was collected at 15 minutes before and 5, 10, 15, 30, 45, 60, 90, 120, 180, 270, 360, and 450 minutes after THC formulation intake, and each labeled as PK samples with the timepoints. THC intake and subsequent blood collection were staggered for each subject.

Each volunteer was assigned a unique code and blinded. Access to this code was strictly controlled; analysts and coordinators did not have access to the code until the study had concluded and all necessary data analysis had been completed.

Figure 3:
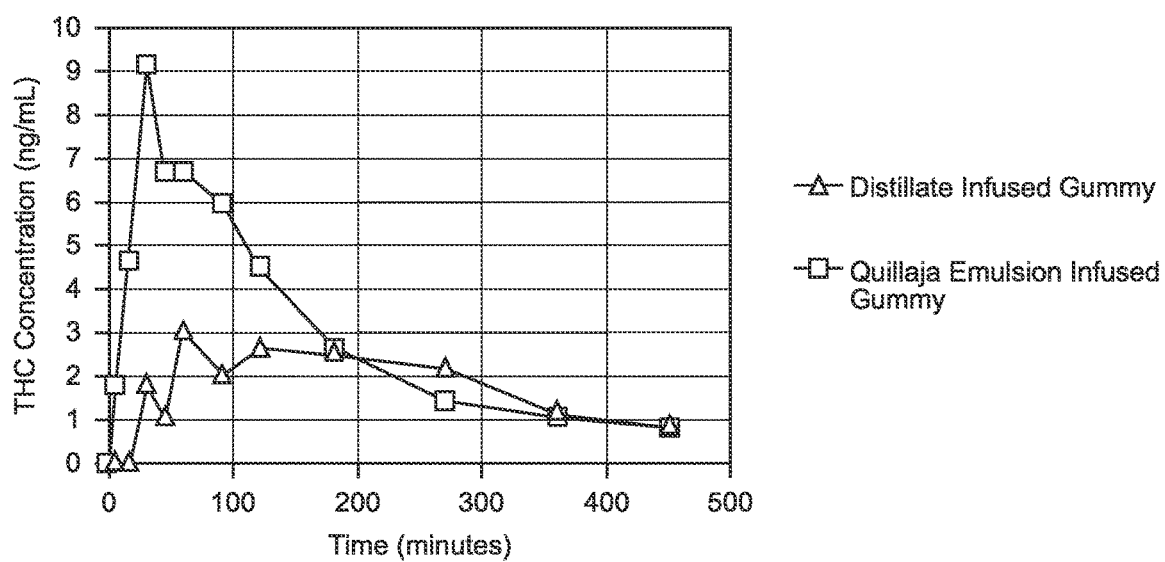
FIG. 3 shows results from a pharmacokinetic study comparing effects of a *Quillaja* extract based emulsion-infused gummy and a distillate-infused gummy.
Figure 4:
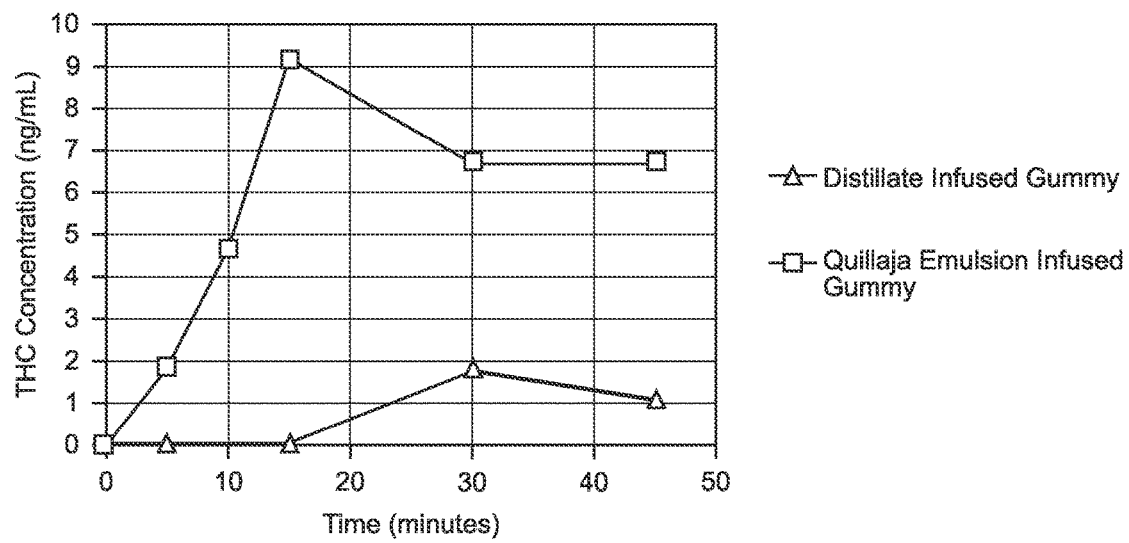
FIG. 4 shows results from a pharmacokinetic experiment comparing effects of a *Quillaja* extract based emulsion-infused gummy and a distillate-infused gummy.

The PK profile of *Quillaja* extract based emulsion infused gummy and distillate infused gummy were plotted in the graphs shown in FIGS. 3 and 4. The graphs show that the *Quillaja* extract based emulsion infused gummy has a much quicker onset and higher bioavailability than distillate infused gummy.

At <30 mins, the *Quillaja* extract based emulsion infused gummy delivered THC into the blood at 5 minutes compared to 30 min delivery for a distillate-infused gummy. This surprising discovery confirms that the emulsion is "fast acting" and has "quick onset".

Based on the published data from Ripple™ and Wana™ gummies from this literature (Ewell, Taylor Russell, et al "Pharmacokinetic Investigation of Commercially Available Edible Marijuana Products in Humans: Potential Influence of Body Composition and Influence on Glucose Control." *Pharmaceuticals* 14.8 (2021): 817.), the raw data for the *Quillaja* extract based emulsion was normalized from 15 mg dosage to 10 mg dosage in order to compare the data. The normalization applied the clearance, elimination rate-constant, and THC half-life published from the literature cited above. The overall data comparison can be found below.

TABLE 15

| | *Quillaja* extract Emulsion Infused gummy | Distillate gummy | Ripple ™ Gummies | Ripple ™ Pure 10 | Ripple ™ Quick Sticks | Wana ™ Fast Acting Gummies | Wana ™ Sour Gummies |
|---|---|---|---|---|---|---|---|
| THC | | | | | | | |
| AUC normalized (ng*min/mL) | 1009.5 | 631.1 | 533 | 447 | 570 | 455 | 406 |
| C-max normalized (ng/mL) | 8.1 | 1.3 | 5.5 | 4.31 | 4.56 | 4.39 | 3.22 |
| T-max (min) | 23 | 100 | 35.7 | 40.7 | 90.7 | 51.4 | 62.1 |
| Early Detection (min) | 7.5 | 30 | 20 | 20 | 20 | 20 | 20 |

TABLE 15-continued

| | Quillaja extract Emulsion Infused gummy | Distillate gummy | Ripple™ Gummies | Ripple™ Pure 10 | Ripple™ Quick Sticks | Wana™ Fast Acting Gummies | Wana™ Sour Gummies |
|---|---|---|---|---|---|---|---|
| 11-OH-THC/THC | 6.9 | 6.9 | 1.64 | 1.35 | 2.06 | 1.53 | 1.68 |
| COOH-THC/THC | 31.6 | 23.1 | 17.1 | 16.06 | 11.76 | 17.02 | 16.43 |
| 11-OH-THC | | | | | | | |
| AUC normalized (ng*min/mL) | 6941.0 | 5892.4 | 816 | 560 | 700 | 669 | 626 |
| C-max normalized (ng/mL) | 35.7 | 10.2 | 6.6 | 5.05 | 5.33 | 5.4 | 4.45 |
| T-max (min) | 60 | 240 | 55.7 | 53.6 | 100.7 | 83.6 | 72.9 |
| 11-COOH-THC | | | | | | | |
| AUC normalized (ng*min/mL) | 31914.7 | 19699.4 | 7047 | 6311 | 6195 | 6467 | 6009 |
| C-max normalized (ng/mL) | 98.5 | 27.1 | 44.0 | 40.24 | 42.25 | 39.36 | 35.78 |
| T-max (min) | 105 | 160 | 105 | 87.9 | 130.7 | 145.7 | 145.7 |

From the perspective of AUC: On average, the *Quillaja* extract emulsion has 37% higher THC bioavailability than distillate, 49% higher THC bioavailability than Ripple™, and 57% higher THC bioavailability than Wana™ products.

From the perspective of T-max: *Quillaja* extract emulsion has T-max of THC at 23 minutes, T-max of 11-0H-THC at 60 minutes and T-max of THC-COOH at 105 minutes. The main active (THC) and all its metabolites all have T-max below 120 minutes On average, the *Quillaja* extract emulsion achieves maximum plasma THC levels 4.4× faster than distillate and 2.5× faster than both the Ripple™ and Wana™ products.

From the perspective of C-max: On average, the *Quillaja* extract emulsion has a 6.4× higher peak plasma THC than distillate, 1.7× higher peak plasma THC than Ripple™ products, and 2.1× higher peak plasma THC than Wana™ products.

Early Detection: Based on the earliest detectable THC in plasma, on average, the *Quillaja* extract emulsion reaches the users bloodstream 4× as quickly as distillate and 2.7× as quickly as both the Ripple™ and Wana™ products.

Ingredients: Caliper® used modified food starch as the emulsifier; Wana™ Fast Acting has modified food starch and xanthan gum in the ingredients. Their current infusion tech is called Azuca™, which is a binding process between cannabinoids and sugar molecule. And then the sugar molecule is added into the gummy process. In this formulation, there is likely no fat molecule such as MCT or LCT that would help the formation of mixed micelle, which is the vehicle to help cannabinoids absorbing into the epithelial cell in the small intestine. This may affect the efficacy and experience of the product.

Ingredients used for Caliper™ gummy: glucose syrup, sugar, water, fruit juice concentrates (apple, pear), gelatin, modified food starch, Ripple™ (water, modified food starch, cannabinoid extracts, MCT oil), contains 2% or less of: natural flavors, malic acid, citric acid, carnauba wax, and vegetable juice for color.

Ingredients used for Wana™ fast-acting gummy: organic cane sugar, organic tapioca syrup, pectin (pectin, potassium sodium tartrate, polyphosphate, sucrose), citric acid, natural flavoring, sodium citrate, modified food starch, xanthan gum, THC.

Example 12

This example provides guidelines for measuring cannabinoid levels in infused edible products. HPLC is usually used to detect cannabinoid concentrations from the infused edibles. Depending on the edible types, different extraction methods may be needed to accurately determine the potency.

For example, for a THC-infused gummy, methanol extraction is often used to extract THC, where pure methanol is used to dissolve and extract THC from the gummy base. The organic layer is then centrifuged or filtered and then diluted to the desired range to be injected into the HPLC column.

However, when the edible base is a chocolate, different cannabinoids have different binding efficiencies towards the fat in the chocolate due to their chemical structural difference. The end results are, when testing the same amount of CBN, CBG, THC, and CBD from the same amount of chocolate, CBN and THC, where they have one hydroxyl group, will be detected less accurately than CBG and CBD, which have two hydroxyl groups. So, when there are fats in the edible matrix, the extraction method needs to be customized against the individual cannabinoid to ensure accurate detection.

Also, when different cannabinoids are infused by emulsion into an edible base, detecting them all at an accurate level can be challenging, especially when certain cannabinoids are at magnitude higher potency level compared to others.

The following table illustrates a specific example of infused gummies, in which a broad-spectrum CBD extract with three minor cannabinoids (CBG, CBN, CBC) was used as the starting input material, but the minor cannabinoids were not detected.

TABLE 16

Certificate of Analysis Results

| Cannabinoids | Broad Spectrum Oil | | Broad Spectrum Emulsion | | Emulsion-Infused Finished Product |
|---|---|---|---|---|---|
| CBD | 89.062% | > | 6.45% | > | 0.31% |
| CBG | 0.278% | | ND | | ND |
| CBN | 0.671% | | ND | | ND |
| CBC | 0.804% | | 0.079% (below LOQ) | | ND |

LOD<0.01% means limit of detection and is the lowest analyte concentration reliably distinguished from the baseline. spectrum.

LOQ<0.025% means limit of quantitation. This means that the lab equipment can detect that the compound is present but the compound is at such a low level that it cannot be accurately quantified.

As indicated in the chart, there are two separate steps that effectively dilute the original distillate:

The first step, from oil to emulsion, can cause an approximately 10× dilution.

The second dilution occurs when the emulsion is infused into the gummy, which can cause another 20× dilution.

While the minor cannabinoids were still present, by the time the finished product was created, they were diluted to a point where they were unable to be detected by standard laboratory testing equipment and procedures. When reviewing the Certificate of Analysis (COA) for the product, using the methods above, it would be indiscernible from a formula that used CBD isolate.

To detect minor cannabinoids more accurately, two modifications can be used:

1. Equipment: For typical, highly concentrated extract potency testing, liquid chromatography with a diode array detector is sufficient. However, for examining minor cannabinoids in an edible matrix, more sensitive laboratory equipment is required. In this case, liquid chromatography coupled with a mass spectrometer (LC/MS/MS) is necessary to accurately quantify the lesser concentrated components.

2. Sample Preparation: In order to accurately quantitate both the major and minor cannabinoids in a single product, multiple separate sample dilutions for respective cannabinoids are necessary to fit all cannabinoids into the calibration range of the instrument.

Utilizing these equipment and method adjustments, Anresco Laboratories™ analyzed a second batch of infused Molly Jones™ gummies with updated LOQ and LOD. Shown in Table below.

TABLE 17

| | Initial Method: LC-DAD | Updated Method: LC/MS/MS |
|---|---|---|
| LOQ | 0.02500% | 0.00015% |
| LOD | 0.01000% | 0.00005% |

Minor cannabinoids in the final product are provided below.

TABLE 18

COA of Oil Undergoing Dilution

| | | Broad Spectrum Oil | Broad Spectrum Emulsion | Initial Method: Gummy Tested With LC-DAD | Updated Method: Gummy Tested with LC/MS/MS |
|---|---|---|---|---|---|
| Cannabinoids | CBD | 89.062% | 6.45% | 0.31% | 0.41% |
| | CBG | 0.278% | ND | ND | 0.002% |
| | CBN | 0.671% | ND | ND | 0.002% |
| | CBC | 0.804% | 0.079% (below LOQ) | ND | 0.006% |

Example 13

Emulsions were tested in ice cream. Only three emulsifiers demonstrated desired texture, physical compatibility with the ice cream base, and palatable flavor and mouth feel: *Quillaja* extract, gum acacia and Polyglyceryl-10 Dipalmitate. All other emulsifiers contributed to a bitter taste or undesirable change in the ice cream texture. Gum acacia emulsion added a smooth mouth feel that unexpectedly made the ice cream taste creamier and richer. *Quillaja* extract emulsion made the ice cream taste crispier while maintaining the original texture. Polyglyceryl 10 Dipalmitate emulsion became a paste when pH reached below 4.1. This feature helped increase the viscosity of certain ice cream types and thus improve the overall experience.

Example 14

For the quick setting pectin gummy described in the detailed description, different types of *Cannabis* emulsions were used to test the compatibility. Those 6 emulsions share the same ingredient ratio and were processed under 30,000 PSI for 1 pass by Microfluidizer.

TABLE 19

| CBD | MCT | Main Emulsifier | Water |
|---|---|---|---|
| 1 | 2 | 1.5 | 10 |

Only *Quillaja* extract and gum acacia-based emulsions were compatible with this quick setting gummy recipe, where the finished gummies have a very quick setting time below 30 minutes and the flavor and color of the gummy are regular with no bitter or off notes. While gummy infused by other emulsion types either showed soft texture, longer setting time, bitter notes or an off-white color. The results of each emulsion and their time of setting is shown in table below.

TABLE 20

| Main Emulsifier | Setting Time | Other Note |
| --- | --- | --- |
| Vitamin E TPGS | 8 hours | Strong bitter note, soft texture |
| Polysorbate 60 | 5 hours | Strong bitter note, soft texture |
| Polyglyceryl-10 Dipalmitate | 2 hours | Bitter note, gummy has white color |
| Span 20 | 2 hours | Gummy texture is soft, not firm structure |
| Gum Acacia | 25 minutes | Firm structure, regular color |
| *Quillaja* Extract | 10 minutes | Firm structure, regular color |

Example 15

The following provides an exemplary method for preparing a hard candy, lozenge, and/or cough drop with sugar:

First, weigh ingredients in Kit #1 (sugar, water and corn syrup) into a pot, then weigh citric acid (either in water solution or powder), flavoring, and emulsion into separate heat stable containers. Place citric acid, flavoring and emulsion into oven or heating chamber at 40° C., place an additional empty large heat stable container in the oven to heat to target temperature. Attach candy thermometer to the side of the pot, make sure the probe is fully submerged in the candy mixture. Turn heat on induction burner to 200° F., and slowly ramp up temperature until thermometer reaches 300° F. (hard crack). Stir occasionally until mixture starts to bubble rapidly, to avoid scorching/burning. Remove citric acid, flavoring, and emulsion as well as empty Pyrex from the heating chamber prior to candy mixture getting to 300° F. Combine citric acid, flavor, and emulsion into warm empty container. Once the candy mixture reaches 300° F., remove it from heat and add it carefully to the container. Allow bubbling to subside, then mix with a rubber spatula until emulsion is evenly mixed throughout. After mixing, pour the mixture over the mold, scraping the inside of the container as well. Using the bench scraper, scrape and smooth the excess mixture over the molds, so that the mixture is evenly distributed. Place the filled mold on a flat surface in a cool dry room and allow to cool to room temperature. Once cooled, invert the mold, and release the candies from the mold, store in a sealed container.

The 6 types of THC emulsions were produced and infused into the sugar based hard candy under the same cooking conditions. The emulsion ingredient ratio was the same. The potency of the hard candy was targeted at 5 mg/5 gram of candy. The hard candy was then compared in terms of flavor, texture, and *Cannabis* experience. The table below shows the general ratio of the 6 emulsions and the comparison of candy properties.

TABLE 21

| THC | MCT | Main emulsifier | Water |
| --- | --- | --- | --- |
| 1 | 2 | 1.5 | 10 |

All emulsion types appeared to work in terms of infusing into the sugar base at 300° F. All emulsions were targeted at the same potency and the same amount of the emulsion was used. Since the infusion steps looked similar, the infused hard candies should be similar. Surprisingly, Vitamin E TPGS, polysorbate 60, Polyglyceryl-10 Dipalmitate and span 20 emulsions infused hard candy had a bitter to very bitter flavor. Polyglyceryl-10 Dipalmitate and Span 20 emulsion-infused hard candy showed a soft texture, indicating the ingredient incompatibility between the emulsifier and hard candy ingredients. Only the gum acacia and *Quillaja* extract emulsions were the best options to be infused into hard candy. The hard candy infused by those two emulsions had good neutral flavor with a firm and stable texture; the onset is less than 10 minutes and they, had the lowest potency loss among all other emulsion types.

TABLE 22

| Main Emulsifier | Flavor | Texture | Onset (minutes) | Potency loss % |
| --- | --- | --- | --- | --- |
| Vitamin E TPGS | Very bitter | Firm | 15 | 20% |
| Polysorbate 60 | Very bitter | Firm | 15 | 30% |
| Polyglyceryl-10 Dipalmitate | Bitter | Soft | 15 | 26% |
| Span 20 | Bitter | Soft | 20 | 24% |
| Gum Acacia | Flavor neutral | Firm and stable | 10 | 15% |
| *Quillaja* Extract | Flavor neutral | Firm and stable | 10 | 8% |

Example 16

Isomalt is a good substitute for sugar, which has a lot of benefits in terms of lowering calories while maintaining flavor. Isomalt has a different tolerance to temperature, thus making the candy process slightly different from real sugar. This example provides exemplary steps for using isomalt.

First, weigh ingredients in Kit #1. (isomalt and water) into a pot. Then weigh citric acid, Flavoring, and emulsion into separate heat stable containers. Place citric acid, flavoring and emulsion into oven or heating chamber at 40° C., place an additional empty large heat stable container in the oven to come to temperature. Attach the candy thermometer to the side of the pot, so the probe is fully submerged in the candy mixture. Turn heat on induction burner to 200° F., and slowly ramp up temperature until thermometer reaches 360° F. (hard crack). Stir occasionally until mixture starts to bubble rapidly, to avoid scorching/burning. Remove citric acid, flavoring, and emulsion as well as the empty Pyrex® from the heating chamber prior to the candy mixture getting to 360° F. Combine citric acid, flavor, and emulsion into the warm empty container. Once the candy mixture reaches 360° F., remove it from heat and add it carefully to the container. Allow bubbling to subside, then mix with a rubber spatula until emulsion is evenly mixed throughout. After mixing, pour the mixture over the mold, scraping the inside of the container as well. Using the bench scraper, scrape and smooth the excess mixture over the molds, so that the mixture is evenly distributed. Place the filled mold on a flat surface in a cool dry room and allow to cool to room temperature. Once cooled, invert the mold, and release the candies from the mold. Store in a sealed container.

Depending on each cannabinoid's heat stability and oxidation tendency, the high heat environment would cause potency decay at various:levels. For example, THC is most likely to be oxidized, CBN is most stable against oxidation, and CBD can be oxidized, but at a much lower rate ($1/10^{th}$ of the rate to THC). Terpenes can be also challenging to infuse into a high-heat environment due to their volatility. This offers the solution to infuse various active compound into a hard candy by emulsion. The table below summarizes the potency loss of cannabinoids and terpenes when infused into an isomalt based candy at 300° F. for 5 minutes and 15 minutes. In both cases, the active was infused by either *Quillaja*-based emulsion or gum acacia-based emulsion.

TABLE 23

| Active Ingredients | Potency loss %: 300° F. for 5 minutes | | Potency loss %: 300° F. for 15 minutes | |
| --- | --- | --- | --- | --- |
| | Infused by *Quillaja* extract emulsion | Infused by gum acacia emulsion | Infused by *Quillaja* extract emulsion | Infused by gum acacia emulsion |
| THC | −15% | −8% | −25% | −16% |
| CBD | −5% | −3% | −4% | −2% |
| CBN | −1% | 0% | −1% | 0% |
| Myrcene | −26% | −10% | −51% | −15% |
| Limonene | −37% | −12% | −69% | −17% |

Example 17

Figure 5:
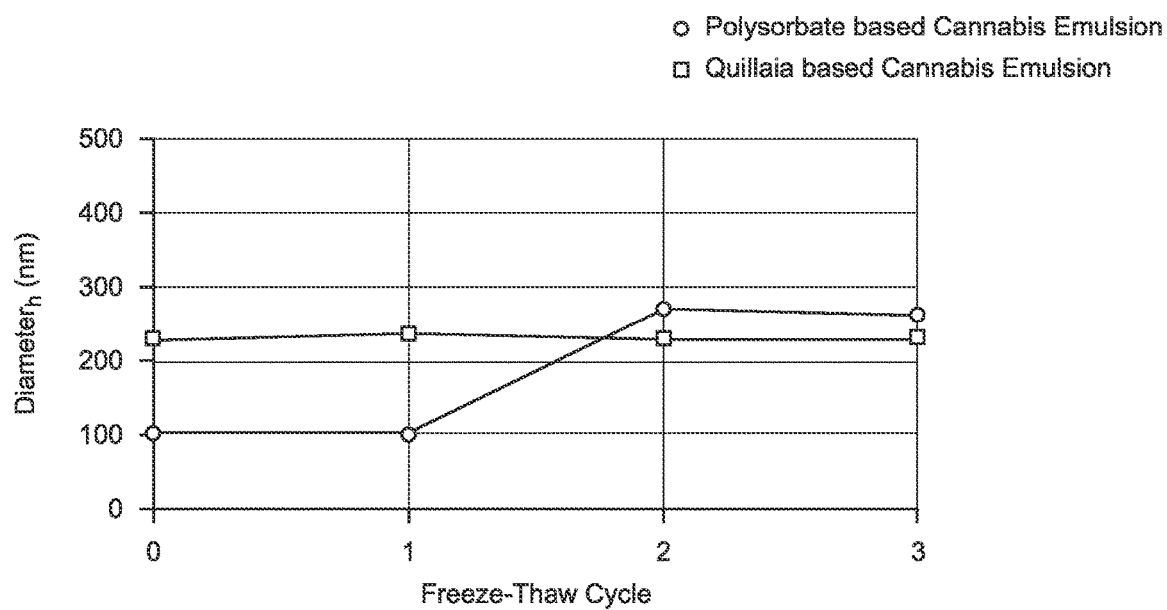
FIG. 5 shows results from a free-thaw stability study.

The use of *Cannabis* emulsion in ice cream and gusher production requires the emulsion to be stable at a low temperature, which can be demonstrated by the freeze-thaw stability of the emulsion. Experiments showed that only *Quillaja* extract based emulsion offered a great freeze-thaw stability with no droplet size change under 3 cycles. Other types of *Cannabis* emulsion such as polysorbate-based emulsion showed significant droplet size growth after 2 freeze-thaw cycle (See FIG. 5).

Another surprising finding is the *Quillaja* extract and gum acacia emulsions offered a similar melting rate with ice cream's original base, whereas other emulsifiers such as Vitamin E TPGS Span 60 accelerated the melting process of the infused ice cream by 2 minutes.

Example 18

Products like hard candies, lozenges, and cough drops last in the mouth for about 1-3 minutes. Sometimes, when using slow melting material, the products may stay in the mouth for over 5 minutes. Longer contact time delivers a higher total bioavailability. The products need to have a high starting potency to create this potency difference so that the diffusion of the active agent can diffuse into the epithelial cell. As for shape, oval or sphere can be the best to offer the highest surface area compared to other shapes, Thus, the *Cannabis*-infused candy, lozenges and cough drop should have these features to achieve a quick onset and high rate of delivery.

Figure 6:
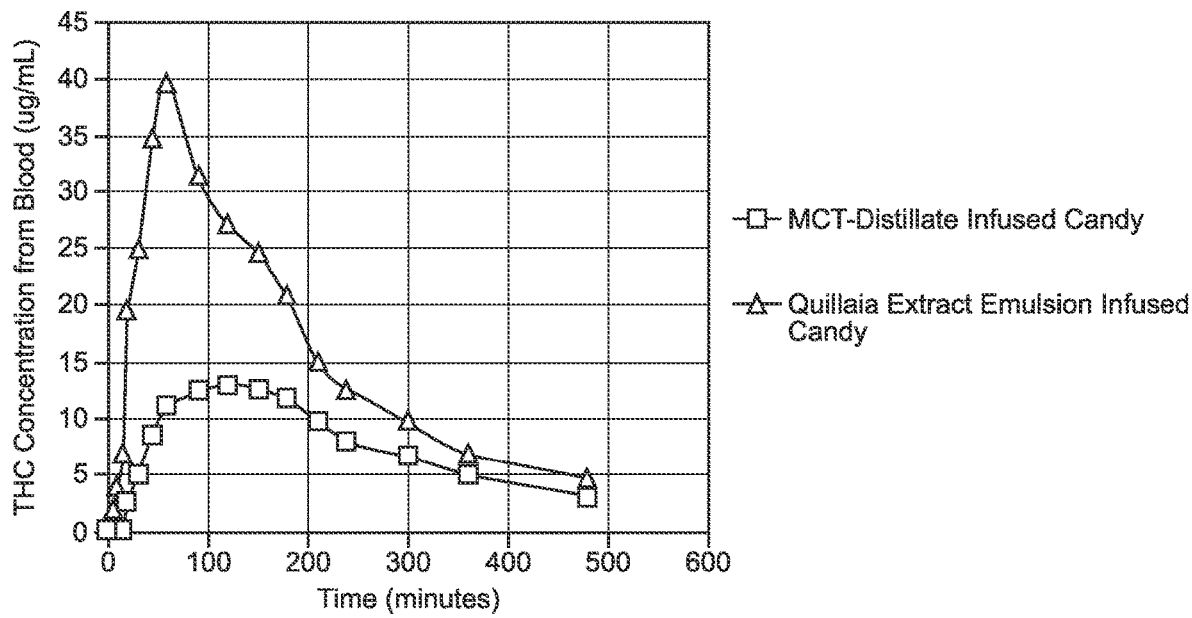
FIG. 6 shows results from a bioavailability study of different infused candies.

When a cannabinoid is infused into a hard candy by MCT oil, it should offer a faster onset experience due to the concentration gradient between the candy and epithelial cell. Experiments surprisingly showed that the experience onset and the blood. PK work showed a much slower onset from MCT-distillate infused candy compared to *Quillaja* extract or gum acacia emulsion infused candies. THC was used as the target and produced THC/MCT infused candy with THC *Quillaja* extract emulsion infused candy and the experience and PK data was compared. Both candy types were targeted at 1.0 mg/3 g candy. The emulsion infused candy dramatically shortened the T-max by 60 minutes, cutting down the time needed for THC to be detected in blood from 20 minutes to 5 minutes, which in term offered a faster onset experience (5 minutes). Also, the overall bioavailability increased nearly 3-fold. (See FIG. 6).

TABLE 24

| Parameter | *Quillaja* Extract Emulsion Infused Candy | MCT-Distillate Formula Infused Candy |
| --- | --- | --- |
| Average Onset | 5 minutes | 35 minutes |
| T-max | 60 minutes | 120 minutes |
| Time before detected in blood | 5 minutes | 20 minutes |
| C-max | 39.7 ug/mL | 15.6 ug/mL |

Example 19

Figure 7:
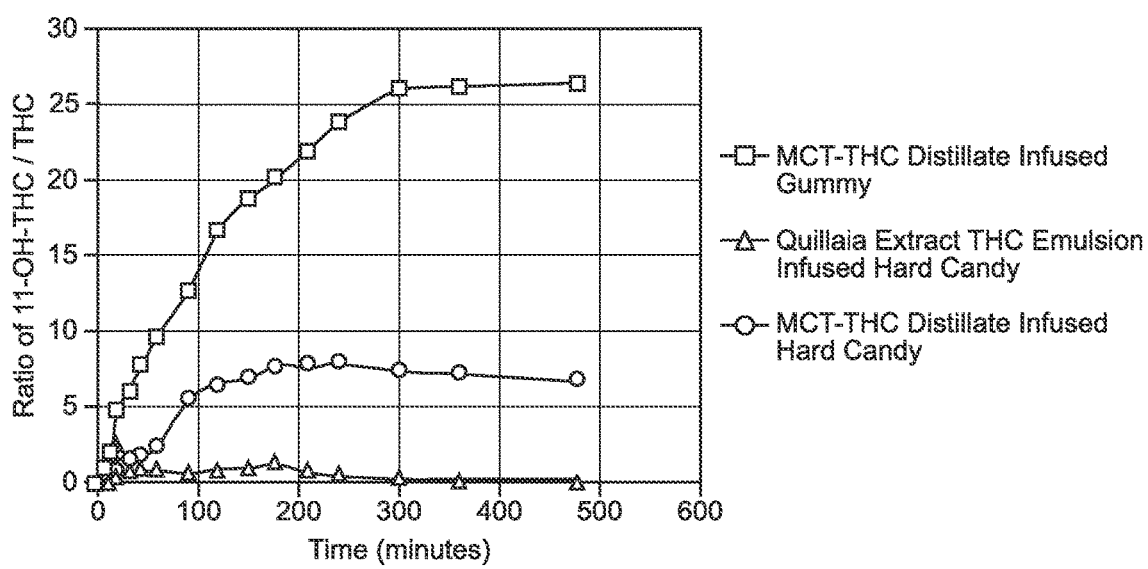
FIG. 7 shows results from experiments testing liver metabolism of different edible products.

By-passing the liver can be an important feature, where different kinds of active agents can be delivered into the systematic circulation without being metabolized into uncontrolled molecules. For example, if 5:3 ratio of THC:CBN is designed to deliver a sleeping effect, liver will metabolize the THC into 11-hydroxy THC and CBN into 11-hydroxy CBN and 8-hydroxy CBN. The effects of the original compound are usually different from the metabolites, making the experience uncontrolled and unrepeatable. As shown in the FIG. 7, the ratio of 11-OH-THC/THC is measured with three different active agent types, all of which have the same 20 mg/3 g potency but produced by different starting materials: MCT-THC distillate infused gummy, MCT-THC distillate infused hard candy and *Quillaja* extract THC emulsion-infused hard candy. The data showed that when infused with *Quillaja* extract, the hard candy delivered a very low ratio of 11-OH-THC, which indicates by-passing the liver metabolism. The regular gummy infused by MCT-THC distillate showed a very high ratio of 11-OH-THC, which indicates that this version tends to constantly transfer THC through portal vein into liver and get metabolized. Another surprising finding was that the 11-OH-THC became more dominant as time passed. This may indicate that the candy was washed down by saliva and eventually became an edible, which follows the similar trend as the MCT-distillate infused gummy. This surprising finding provides strong evidence that an emulsion-infused hard candy is a great vehicle to deliver API intact, which is the key to design an experience using a combination of cannabinoids and terpenes.

Example 20

To infuse an emulsion into the chewing gum, the preferred emulsifiers are gum acacia, *Quillaja* extract, or Polyglyceryl-10 Dipalmitate. They all offer a palatable infused product with little lingering bitterness coming off the long term of chewing. One key aspect of infusing cannabinoids emulsion into chewing gum is to be released into the mouth mucosal membrane upon chewing. In an in vivo dissolution study, 10 mg CBD was added into the chew gum base by each of the three emulsions. The chewing gum was then placed onto an agitating device to simulate agitation from the mouth, which also contains the liquid to mimic pH, temperature, and enzyme composition in the mouth. After 10 mins of agitation the liquid was analyzed by HPLC to recover CBD. Even though all three emulsions work similarly in the infusion process, *Quillaja* extract and gum acacia infused chewing gum released more CBD than Polyglyceryl-10 Dipalmitate based emulsion.

TABLE 25

|  | CBD recovery % after 10 mins agitation |
|---|---|
| *Quillaja* Extract | 68% |
| Gum Acacia | 61% |
| Polyglyceryl -10 Dipalmitate | 37% |

Example 21

To test for potency homogeneity, 10 individual gummies were taken from the same batch but from different phases of the gummy making process. Experiments were done to compare the distillate-infused gummy and emulsion-infused gummy for potency homogeneity. The gummy potency was targeted at 2.55 mg/g and the result in the Table below shows emulsion infused gummy has very tight potency distribution with a small standard deviation at 0.0097. The distillate infused gummy showed a wider distribution of potency with the standard deviation at 0.0806, almost 8.3 times higher than emulsion infused gummy. For the distillate-infused gummy, the lower potency was 2.44 mg/g and the highest potency was 2.69 mg/g, which is a 10.2% difference. This is enough to affect the consistency of the infused product.

TABLE 26

|  | Potency of each gummy (mg/g) | |
|---|---|---|
| Gummy Tested | Emulsion-infused gummy | Distillate-infused gummy |
| 1 | 2.55 | 2.59 |
| 2 | 2.54 | 2.69 |
| 3 | 2.56 | 2.48 |
| 4 | 2.57 | 2.49 |
| 5 | 2.56 | 2.61 |
| 6 | 2.55 | 2.53 |
| 7 | 2.56 | 2.47 |
| 8 | 2.54 | 2.49 |
| 9 | 2.55 | 2.44 |
| 10 | 2.56 | 2.61 |
| Average | 2.554 | 2.54 |
| Standard Deviation | 0.0097 | 0.0806 |

Example 22

*Quillaja* extract, gum acacia and Polyglyceryl-10 Dipalmitate emulsions were tested in the ice cream beads product (e.g., Dippin' Dots™), where the emulsion was mixed into the base prior to −80° C. treatment. Post the cryo-treatment, the product was compared to un-infused control sample, no obvious change in flavor and color of the product. The gum acacia emulsion provided a more smooth/soft mouthfeel while *Quillaja* extract emulsion provided a more clean crisp mouthfeel, Polyglyceryl-10 Dipalmitate did not too much change in the mouthfeel. All three emulsions reached the target potency without seeing any additional potency loss during the process suggesting that all three emulsions work in this product.

The various methods and techniques described above provide a number of ways to carry out the application. Of course, it is to be understood that not necessarily all objectives or advantages described are achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by including one, another, or several other features.

Furthermore, the skilled artisan will recognize the applicability of various features from different embodiments. Similarly, the various elements, features and steps discussed above, as well as other known equivalents for each such element, feature, or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, any numbers expressing quantities of ingredients, properties such as molecular weight, reaction conditions, and so forth, used to describe and claim certain embodiments of the disclosure are to be understood as being modified in some instances by the term "about." Accordingly, in some embodiments, the numerical parameters set forth in the written description and any included claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are usually reported as precisely as practicable.

In some embodiments, the terms "a" and "an" and "the" and similar references used in the context of describing a particular embodiment of the application (especially in the context of certain claims) are construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Variations on preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A packaged gummy infused with a Quillaja based *cannabis* emulsion consisting essentially of distilled or isolated delta-9-tetrahydrocannabinol and/or distilled or isolated cannabidiol; an oil selected from the group consisting of sunflower oil, olive oil, coconut oil, avocado oil, palm oil, soybean oil, corn oil, peanut oil, canola oil, grape seed oil, hazelnut oil, rice bran oil, linseed oil, safflower oil, sesame oil, passion fruit oil, and medium chain triglyceride; vitamin E; gelatin or pectin; and water.

2. The packaged gummy of claim 1, wherein the oil is medium chain triglyceride, coconut oil, olive oil, safflower oil, or sunflower oil.

3. The packaged gummy of claim 2, wherein the oil is medium chain triglyceride.

4. The packaged gummy of claim 1, wherein gelatin is in the gummy.

5. The packaged gummy of claim 1, wherein pectin is in the gummy.

* * * * *